US012714728B2

(12) United States Patent
Himmerich et al.

(10) Patent No.: US 12,714,728 B2
(45) Date of Patent: Aug. 25, 2026

(54) METHODS FOR THE PRODUCTION OF CARDIAC FIBROBLASTS

(71) Applicants: FUJIFILM Cellular Dynamics, Inc., Madison, WI (US); FUJIFILM Holdings America Corporation, Valhalla, NY (US)

(72) Inventors: Sarah Himmerich, Madison, WI (US); Nathaniel Beardsley, Madison, WI (US); Annie Armstrong Smelter, Madison, WI (US); Nathan Meyer, Madison, WI (US); Ravi Vaidyanathan, Madison, WI (US); Cara Rieger, Madison, WI (US)

(73) Assignees: FUJIFILM Cellular Dynamics, Inc., Madison, WI (US); FUJIFILM Holdings America Corporation, Valhalla, NY (US)

( * ) Notice: Subject to any disclaimer, the term of this patent is extended or adjusted under 35 U.S.C. 154(b) by 308 days.

(21) Appl. No.: 18/479,774

(22) Filed: Oct. 2, 2023

(65) Prior Publication Data

US 2024/0139256 A1 May 2, 2024

Related U.S. Application Data

(60) Provisional application No. 63/412,212, filed on Sep. 30, 2022.

(51) Int. Cl.

| | |
|---|---|
| ***C12N 5/077*** | (2010.01) |
| ***A61K 35/33*** | (2015.01) |
| ***A61P 9/04*** | (2006.01) |
| ***C12N 5/071*** | (2010.01) |

(52) U.S. Cl.

CPC ................ *A61K 35/33* (2013.01); *A61P 9/04* (2018.01); *C12N 5/0657* (2013.01); *C12N 5/0697* (2013.01); *C12N 2501/115* (2013.01); *C12N 2501/155* (2013.01); *C12N 2501/16* (2013.01); *C12N 2501/415* (2013.01); *C12N 2506/45* (2013.01)

(58) Field of Classification Search

None

See application file for complete search history.

(56) References Cited

U.S. PATENT DOCUMENTS

| | | | |
|---|---|---|---|
| 10,711,246 | B2 | 7/2020 | Keller et al. |
| 11,072,780 | B2 | 7/2021 | Kamp et al. |
| 2012/0129211 | A1 | 5/2012 | Kattman et al. |
| 2013/0189785 | A1 | 7/2013 | Palecek et al. |
| 2015/0152389 | A1 | 6/2015 | Palecek et al. |
| 2016/0215263 | A1 | 7/2016 | Keller et al. |
| 2017/0002325 | A1 | 1/2017 | Palecek et al. |
| 2017/0037375 | A1 | 2/2017 | Palecek et al. |
| 2018/0094245 | A1 | 4/2018 | Kamp et al. |
| 2019/0085293 | A1 | 3/2019 | Palecek et al. |
| 2021/0254009 | A1 | 8/2021 | Iwamiya |
| 2022/0348877 | A1 | 11/2022 | Wu et al. |

FOREIGN PATENT DOCUMENTS

| | | |
|---|---|---|
| EP | 2318520 | 5/2011 |
| EP | 3044310 | 7/2016 |
| WO | WO 2015-035506 | 3/2015 |
| WO | WO 2015-042356 | 3/2015 |
| WO | WO 2018-232458 | 12/2018 |
| WO | WO 2020-264308 | 12/2020 |
| WO | WO 2021-090031 | 5/2021 |
| WO | WO 2021-186044 | 9/2021 |
| WO | WO 2022-261330 | 12/2022 |

OTHER PUBLICATIONS

Guadix et al., Stem Cell Reports, vol. 9, 1754-1764, 2017 (Year: 2017).*

Guadix et al., Stem Cell Reports, vol. 9, 1754-1764, 2017, Supplemental Information, 10 pages (Year: 2017).*

Steele-Stellard et al., Frontiers in Physiology, Oct. 2018, vol. 9, Article 1332, 19 pages (Year: 2018).*

Van den Heuvel-Eibrink MM, editor. Wilms Tumor. Chap13 WT1 in Cardiac Development and Disease, Brisbane (AU): Codon Publications; Mar. 2016, avail at: https://www.ncbi.nlm.nih.gov/books/NBK373348/#:~:text=Within%20the%20initial%20stages%20of,a%20functional%20contractile%20cardiac%20wall. (Year: 2016).*

Archer et al., "Characterization and validation of a human 3D cardiac microtissue for the assessment of changes in cardiac pathology," *Scientific Reports,* 8:10160, 2018.

Floy et al., "Directed differentiation of human pluripotent stem cells to epicardial-derived fibroblasts," *Star Protocols,* 3(2):101275, 2022.

Giacomelli et al., "Human-iPSC-derived cardiac stromal cells enhance maturation in 3D cardiac microtissues and reveal non-cardiomyocyte contributions to heart disease," *Cell Stem Cell,* 26(6):862-879, 2020.

Guo and Pu, "Cardiomyocyte maturation—New Phase in Development," *Circulation Research,* 126:1086-1106, 2020.

Lee et al., "Human pluripotent stem cell-derived atrial and ventricular cardiomyocytes develop from distinct mesoderm populations," *Cell Stem Cell,* 21(2):179-194, 2017.

PCT International Search Report and Written Opinion issued in International Application No. PCT/US2023/075750, mailed Feb. 5, 2024.

Ravenscroft et al., "Cardiac non-myocyte cells show enhanced pharmacological function suggestive of contractile maturity in stem cell derived cardiomyocyte microtissues," *Toxicological Sciences,* 152(1):99-112, 2016.

(Continued)

*Primary Examiner* — Evelyn Y Pyla

(74) *Attorney, Agent, or Firm* — pH IP Law

(57) ABSTRACT

Provided herein are methods for producing quiescent cardiac fibroblast cells from pluripotent stem cells. Further provided herein are microtissue compositions comprising the cardiac fibroblast cells with endothelial cells and cardiomyocytes.

32 Claims, 25 Drawing Sheets

(56) References Cited

OTHER PUBLICATIONS

Thomas et al., "Fabrication of 3D cardiac microtissue arrays using human iPSC-derived cardiomyocytes, cardiac fibroblasts, and endothelial cells," *Journal of Visualized Experiments,* 169:e61879, 2021.
Whitehead et al., "Improved epicardial cardiac fibroblast generation from iPSCs," *Journal of Molecular and Cellular Cariology,* 164:58-68, 2022.
Zhang et al., "Functional cardiac fibroblasts derived from human pluripotent stem cells via second heart filed progenitors," *Nature Communications,* 10(1):2238, 2019.

* cited by examiner

DBL CHIR
DB CHIR ACT
11713 310b
11713 310b ACT
primary human SMC

FOLD TO GAPDH 10.00
1.00
0.10
0.01
0.00

POSTN
VIM
DDR2
COL1A1
COL1A2
GJA1
ACTA2

GENE

| Name | ID | # of cells in population with expression >0 | % of cells in population with expression >0 |
|---|---|---|---|
| VIM | ENSG00000026025 | 6676 | 100% |
| TPM1 | ENSG00000140416 | 6576 | 100% |
| ITGB1 | ENSG00000150093 | 6575 | 100% |
| TIMP1 | ENSG00000102265 | 6569 | 100% |
| TAGLN | ENSG00000149591 | 6566 | 100% |
| CAV1 | ENSG00000105974 | 6526 | 99% |
| FN1 | ENSG00000115414 | 6503 | 99% |
| COL1A1 | ENSG00000108821 | 6395 | 97% |
| SPARC | ENSG00000113140 | 6288 | 95% |
| COL1A2 | ENSG00000164692 | 6223 | 95% |
| CDH2 | ENSG00000170558 | 6077 | 92% |
| NR2F2 | ENSG00000185551 | 6037 | 92% |
| MMP2 | ENSG00000087245 | 5973 | 91% |
| CTGF | ENSG00000118523 | 5660 | 86% |
| DKK3 | ENSG00000050165 | 5200 | 79% |
| KRT19 | ENSG00000171345 | 4998 | 76% |
| TGFB1 | ENSG00000105329 | 4837 | 74% |
| DDR2 | ENSG00000162733 | 4627 | 70% |
| MEF2A | ENSG00000068305 | 4436 | 67% |
| TBX3 | ENSG00000135111 | 4245 | 65% |
| CDH11 | ENSG00000140937 | 3969 | 60% |
| THY1 | ENSG00000154096 | 3850 | 59% |
| TWIST1 | ENSG00000122691 | 3784 | 58% |
| S100A4 | ENSG00000196154 | 3559 | 54% |
| GJA1 | ENSG00000152661 | 3117 | 47% |
| TRPM7 | ENSG00000092439 | 3091 | 47% |
| HAND2 | ENSG00000164107 | 3085 | 47% |
| GATA4 | ENSG00000136574 | 3053 | 46% |
| SOX17 | ENSG00000164736 | 3007 | 46% |
| MCAM | ENSG00000076706 | 2866 | 44% |
| CNN1 | ENSG00000130176 | 2635 | 40% |
| ACTA2 | ENSG00000107796 | 2507 | 38% |
| MEF2C | ENSG00000081189 | 2398 | 36% |
| TGFB2 | ENSG00000092969 | 2378 | 36% |
| MMP1 | ENSG00000196611 | 2250 | 34% |
| TEK | ENSG00000120156 | 2170 | 33% |
| RORA | ENSG00000069667 | 2037 | 31% |
| PDGFRB | ENSG00000113721 | 1985 | 30% |

FIG. 4H

| | | | |
|---|---|---|---|
| TTK | ENSG00000112742 | 1922 | 29% |
| GJC1 | ENSG00000182963 | 1824 | 28% |
| MEF2D | ENSG00000116604 | 1788 | 27% |
| PDGFRA | ENSG00000134853 | 1637 | 25% |
| POSTN | ENSG00000133110 | 1433 | 22% |
| CSPG4 | ENSG00000173546 | 1418 | 22% |
| GJA1 | ENSG00000152661 | 1355 | 21% |
| TIE1 | ENSG00000066056 | 1334 | 20% |
| SNAI1 | ENSG00000124216 | 1114 | 18% |
| PITX2 | ENSG00000164093 | 960 | 14% |
| WT1 | ENSG00000184937 | 946 | 14% |
| TBX18 | ENSG00000112837 | 745 | 11% |
| KDR | ENSG00000128052 | 598 | 9% |
| TBX20 | ENSG00000164532 | 589 | 9% |
| PECAM1 | ENSG00000261371 | 572 | 9% |
| TBX5 | ENSG00000089225 | 487 | 7% |
| CDH2 | ENSG00000170558 | 428 | 7% |
| TBX2 | ENSG00000121068 | 413 | 6% |
| CACNA1C | ENSG00000151067 | 393 | 6% |
| GATA6 | ENSG00000141448 | 288 | 4% |
| DCN | ENSG00000011465 | 255 | 4% |
| IL6 | ENSG00000136244 | 249 | 4% |
| BMP4 | ENSG00000125378 | 233 | 4% |
| LUM | ENSG00000139329 | 224 | 3% |
| PAX3 | ENSG00000135903 | 197 | 3% |
| TRPC3 | ENSG00000138741 | 192 | 3% |
| MYH11 | ENSG00000133392 | 170 | 3% |
| RGS5 | ENSG00000232995 | 141 | 2% |
| TCF21 | ENSG00000118526 | 138 | 2% |
| HEY1 | ENSG00000164683 | 137 | 2% |
| PDPN | ENSG00000162493 | 139 | 2% |

FIG. 4H cont.

METHODS FOR THE PRODUCTION OF CARDIAC FIBROBLASTS

PRIORITY CLAIM

This application claims benefit of priority to U.S. Provisional Application Ser. No. 63/412,212 filed Sep. 30, 2022, the entire contents of which are hereby incorporated by reference.

BACKGROUND

1. Field

The present invention relates generally to the field of molecular biology. More particularly, it concerns the differentiation of pluripotent stem cells to cardiac fibroblasts.

2. Description of Related Art

It is well known that most pluripotent stem cell derived cardiomyocytes (PSC-CM) have an immature phenotype and are more closely related to fetal cardiomyocytes than adult cardiomyocytes in cellular structure, calcium handling, metabolism, contractile function, and gene expression. This maturation bottleneck impairs the use of PSC-CM for in vitro modeling for diseases, drug discovery, or cell therapy (Guo and Pu et al., 2020).

Recent studies show that cardiac supporting cell types play an important role in cardiomyocyte development, maturation, and cardiovascular disease. Multi-cellular microtissue models combining PSC-CM with primary human cardiac fibroblasts and primary human endothelial cells in scaffold-free microtissues displayed a more relevant "mature" response in compound testing, including an inotropic response to isoproterenol (Ravenscroft, 2016). A similar model has also been used for high-throughput screening of structural cardiotoxins (Archer, 2018).

Most researchers who desire to form a multicellular cardiac microtissue may use one or more cell types from induced pluripotent stem cells. Substituting isogenic PSC-derived supporting cell types for primary human cells offers many benefits to improving the relevance and reproducibility of the cardiac multi-cellular microtissue model (Giacomelli, 2022). However, the need to differentiate all three cell types from iPSC and synchronize culture of the cell types before combining in the microtissue limits the application of the cardiac microtissue assay platform. Thus, there is an unmet need for a cardiac microtissue assay platform assembled from three isogenic purified, cryopreserved PSC-derived cell types (i.e., cardiomyocytes, endothelial cells, and cardiac fibroblasts) and co-culture medium.

SUMMARY

In certain embodiments, the present disclosure provides an in vitro method for producing human pluripotent stem cell (PSC)-derived cardiac progenitor cells comprising (a) culturing PSC aggregates in media comprising a Wnt agonist, Activin agonist, and BMP4 for mesoderm induction; (b) further culturing the PSC aggregates in media comprising an Activin agonist and BMP4 and essentially free of a Wnt agonist to produce a population of NCAM positive and CXCR4 low mesoderm progenitor cells; and (c) culturing the mesoderm progenitor cells in media comprising a Wnt inhibitor to produce a population of cardiac progenitor cells. In some aspects, step (c) is further defined as producing a mixed population of cardiac progenitor cells and cTNT+ cardiomyocytes. In certain aspects, the method further comprises producing PSC-derived cardiac fibroblasts comprising differentiating the cardiac progenitor cells to produce a population of cardiac fibroblasts in media comprising basic FGF (bFGF). In some aspects, the differentiating to cardiac fibroblasts is performed in the absence of a TGFβ inhibitor.

A further embodiment provides an in vitro method for producing human pluripotent stem cell (PSC)-derived cardiac fibroblasts comprising (a) culturing PSC aggregates in media comprising a Wnt agonist, Activin agonist, and BMP4 for mesoderm induction; (b) further culturing the PSC aggregates in media comprising an Activin agonist and BMP4 and essentially free of a Wnt agonist to produce a population of NCAM positive and CXCR4 low mesoderm progenitor cells; (c) culturing the mesoderm progenitor cells in media comprising a Wnt inhibitor to produce a population of cardiac progenitor cells; and (d) differentiating the cardiac progenitor cells to produce a population of cardiac fibroblasts in media comprising basic FGF (bFGF).

In some aspects, the mesoderm progenitor cells are positive for NCAM and have low expression of CXCR4 (NCAM+/CXCR4$^{low}$). In specific aspects, less than 10% (e.g., less than 5%) of the mesoderm progenitor cells are positive for CXCR4.

In certain aspects, the cardiac progenitor cells comprise epicardial progenitor cells, endothelial fibroblast progenitor cells, second heart field progenitors, and/or neural crest progenitor cells. In some aspects, about 30% to 70% (e.g., 30-50%, 40-60%, 50-70%, about 30%, about 40%, about 50%, about 60%, or about 70%) of the cardiac progenitors cells are second heart field progenitor cells, such as cells positive for GATA4 and/or HAND2. In certain aspects, about 10-50% (e.g., 10-30%, 20-40%, 30-50%, about 10%, 20%, 30%, 40%, or 50%) of the cardiac progenitor cells are endothelial fibroblast progenitor cells, such as cells positive for TEK. In some aspects, about 5-40% (e.g., 5-15%, 10-20%, 15-30%, 20-40%, about 5%, 10%, 15%, 20%, 30%, or 40%) of the cardiac progenitor cells are epicardial progenitor cells, such as cells positive for WT1, SNAIL TBX19, and/or TBX20. In some aspects, the cardiac progenitor cells are oligopotent. In some aspects, the cardiac fibroblasts express vimentin (VIM), COL1A1, COL1A2, and/or secreted protein acidic and rich in cysteine (SPARC). In some aspects, the cardiac fibroblasts express discoidin domain receptor 2 (DDR2) and periostin (POSTN). In some aspects, the cardiac fibroblasts are at least 40% (e.g., at least 40%, 45%, 50%, 55%, 60%, 70%, 80%, 85%, 90%, 95%, or 100%) positive for GATA-4. In certain aspects, the cardiac fibroblasts are at least 50%, such as at least 60%, 70%, 80%, 85%, 90%, 95%, 99%, or 100% positive for CD90.

In some aspects, the PSCs are induced pluripotent stem cells (iPSCs) or embryonic stem cells (ESCs). In certain aspects, the iPSCs are derived from a normal healthy subject or a subject with a genetic disease genotype. In certain aspects, the iPSCs are engineered to comprise a disease-relevant mutation for cardiovascular disease. In some aspects, the iPSCs are derived from a subject with dilated cardiomyopathy and comprise an LMNA-L35P mutation.

In certain aspects, the Wnt agonist of step (a) is CHIR 99021, SB216763, CHIR 98014, TWS119, Tideglusib, SB415286, BIO, AZD2858, AZD1080, AR-A014418, TDZD-8, LY2090314, or IM-12. In particular aspects, the Wnt agonist is CHIR 99021. In some aspects, the CHIR 99021 is present in step (a) at a concentration of about 5 μM to 10 μM, such as 5 μM, 6 μM, 7 μM, 8 μM, 9 μM, or 10 μM. In some aspects, the CHIR 99021 is present in step (a) at a concentration of about 1 μM to about 20 μM, such as 1-5 μM, 5-10 μM, 10-15 μM, or 15-20 μM.

In certain aspects, the media of steps (a)-(c) do not comprise or have essentially no insulin. In certain aspects, the Activin agonist is Activin A. In some aspects, the media of step (a) further comprises albumin. In certain aspects, the media of any of steps (a)-(c) further comprises albumin.

In some aspects, the PSC aggregates of step (a) were obtained by culturing PSCs in the presence of a Wnt agonist and a survival agent. In some aspects, the Wnt agonist is CHIR 99021, SB216763, CHIR 98014, TWS119, Tideglusib, SB415286, BIO, AZD2858, AZD1080, AR-A014418, TDZD-8, LY2090314, or IM-12. In particular aspects, the Wnt agonist is CHIR 99021. In some aspects, the CHIR 99021 is present in step (a) at a concentration of about 0.5 to 5 μM, such as about 1 μM to 3 μM, such as 1 μM, 2 μM, or 3 μM. In certain aspects, the survival agent is a Rho-associated kinase (ROCK) inhibitor or myosin II inhibitor. In some aspects, the ROCK inhibitor is H1152 or Y-27632. In certain aspects, the myosin II inhibitor is H1152.

In certain aspects, the mesoderm progenitor cells are dissociated into essentially single cells prior to step (c). In some aspects, the media of step (c) is free of or essentially free of BMP4, a Wnt agonist, and retinoic acid. In certain aspects, Wnt inhibitor of step (c) is XAV939, IWR1, IWR2, IWR3, IWR4, ICG-001, IWR-1-endo, Wnt-059, LGK-974, LF3, CP21R7, NCB-0846, PNU-74654, or KYA179K. In some aspects, the Wnt inhibitor is XAV939. In certain aspects, the XAV939 is present in the media at a concentration of 0.5 μM to 10 μM, such as 1 μM to 5 μM, such as 1 μM, 2 μM, 3 μM, 4 μM, or 5 μM.

In some aspects, the population of cardiac progenitor cells in step (c) comprise at least 30% (e.g., 35%, 40%, 45%, 50%, 55%, 60%, 65%, 70%, 75%, 80%, 85%, 90%, 95%, 99% or more) WT1+ progenitor cells. In certain aspects, the population of cardiac progenitor cells in step (c) comprise less than 80% (e.g., less than 85%, 90%, 95%, 98%, 99%, or 100%, such as less than 75%, 70%, 65%, 60%, 50%, or 40%) WT1+ progenitor cells.

In certain aspects, the method does not comprise a purification step between step (c) and differentiating the cells to cardiac fibroblasts. In some aspects, the purification step is further defined as cell sorting.

In particular aspects, the TGFβ inhibitor is SB431542, LDN-193189, LY2157299, LY2109761, SB525334, SIS HCl, SB505124, GW788388, or LY364947. In specific aspects, the TGFβ inhibitor is SB431542. In some aspects, the SB431542 is present in the media at a concentration of 1 μM to 10 μM, such as 1-5 μM, 5-10 μM, 1-3 μM, 3-7 μM, or 7-10 μM.

In certain aspects, the media of step (a) is free of or essentially free of a Wnt agonist and Wnt inhibitor. In some aspects, the media of step (b) is free of or essentially free of TGFβ inhibitor. In certain aspects, the media of step (b) further comprises serum.

In certain aspects, the bFGF is present in the media at a concentration of 50-200 ng/mL. In some aspects, the media of step (b) is free of or essentially free of serum. In particular aspects, the bFGF is present in the media at a concentration of 10-100 ng/mL. In further aspects, the media further comprises VEGF, EGF, and/or IGF.

In some aspects, the population of cardiac fibroblasts comprises at least 75% (e.g., 80%, 85%, 90%, 95%, 99%, or 100%) cells positive for TE-7, CD29, and/or CD90. In certain aspects, the population of cardiac fibroblasts comprises at least 85% cells positive for TE-7 and/or CD29/CD90.

In particular aspects, the cardiac fibroblasts are quiescent cardiac fibroblasts. In some aspects, the population of cardiac fibroblasts comprises less than 15%, 10%, or 5% (e.g., 4%, 3%, 2%, 1% or less) cells positive for alpha smooth muscle actin (αSMA). In some aspects, the population of cardiac fibroblasts comprises at least 85% cells positive for TE-7, CD90, and CD29 and less than 5% cells positive for αSMA.

In additional aspects, the method further comprises cryopreserving the population of cardiac fibroblasts.

In some aspects, the method further comprises culturing the population of cardiac fibroblasts in the presence of TGFβ to produce a population of activated cardiac fibroblasts. In some aspects, the TGFβ is present at a concentration of 10-100 ng/mL, such as 10-25, 25-50, 50-75, or 75-100 ng/mL. In some aspects, the population of activated fibroblasts exhibit increased fibronectin secretion and/or increased expression of αSMA as compared to the population of cardiac fibroblasts prior to culturing in the presence of TGFβ.

In certain aspects, the culture is performed in defined media. In particular aspects, the method is good manufacturing practice (GMP)-compliant.

In certain embodiments, the present disclosure provides an in vitro method for producing human pluripotent stem cell (PSC)-derived epicardial progenitor cells comprising (a) culturing PSC aggregates in media comprising a Wnt agonist, Activin agonist, and BMP4 for mesoderm induction; (b) further culturing the PSC aggregates in media comprising an Activin agonist and BMP4 and essentially free of a Wnt agonist to produce a population of NCAM+/CXCR4+ (e.g., cells positive for NCAM and low expression of CXCR4) mesoderm progenitor cells; and (c) culturing the mesoderm progenitor cells in media comprising a Wnt inhibitor to produce a population of WT+ epicardial progenitor cells. In some aspects, step (c) is further defined as producing a mixed population of WT1+ epicardial progenitor cells and cTNT+ cardiomyocytes. In certain aspects, the method further comprises producing PSC-derived cardiac fibroblasts comprising (a) culturing the WT1+ epicardial progenitor cells in media comprising a TGFβ inhibitor; and (b) differentiating the WT1+ epicardial progenitor cells to produce a population of cardiac fibroblasts in media comprising basic FGF (bFGF). In certain aspects, the method further comprises producing PSC-derived cardiac fibroblasts comprising differentiating the WT1+ epicardial progenitor cells to produce a population of cardiac fibroblasts in media comprising basic FGF (bFGF). In some aspects, the differentiating to cardiac fibroblasts is performed in the absence of a TGFβ inhibitor.

A further embodiment provides an in vitro method for producing human pluripotent stem cell (PSC)-derived cardiac fibroblasts comprising (a) culturing PSC aggregates in media comprising a Wnt agonist, Activin agonist, and BMP4 for mesoderm induction; (b) further culturing the PSC aggregates in media comprising an Activin agonist and BMP4 and essentially free of a Wnt agonist to produce a population of NCAM+/CXCR4+(e.g., NCAM+ $CXCR4^{low\ positive}$) mesoderm progenitor cells; (c) culturing the mesoderm progenitor cells in media comprising a Wnt inhibitor to produce a population of WT+ epicardial progenitor cells; (d) culturing the WT1+ epicardial progenitor cells in media comprising a TGFβ inhibitor; and (e) differentiating the WT1+ epicardial progenitor cells to produce a population of cardiac fibroblasts in media comprising basic FGF (bFGF).

In some aspects, the mesoderm progenitor cells are positive for NCAM and have low expression of CXCR4 (NCAM+/CXCR4$^{low}$). In specific aspects, less than 10% (e.g., less than 5%) of the mesoderm progenitor cells are positive for CXCR4.

In some aspects, the PSCs are induced pluripotent stem cells (iPSCs) or embryonic stem cells (ESCs). In certain aspects, the iPSCs are derived from a normal healthy subject or a subject with a genetic disease genotype. In certain aspects, the iPSCs are engineered to comprise a disease-relevant mutation for cardiovascular disease. In some aspects, the iPSCs are derived from a subject with dilated cardiomyopathy and comprise an LMNA-L35P mutation.

In certain aspects, the Wnt agonist of step (a) is CHIR 99021, SB216763, CHIR 98014, TWS119, Tideglusib, SB415286, BIO, AZD2858, AZD1080, AR-A014418, TDZD-8, LY2090314, or IM-12. In particular aspects, the Wnt agonist is CHIR 99021. In some aspects, the CHIR 99021 is present in step (a) at a concentration of about 5 μM to 10 μM, such as 5 μM, 6 μM, 7 μM, 8 μM, 9 μM, or 10 μM. In some aspects, the CHIR 99021 is present in step (a) at a concentration of about 1 μM to about 20 μM, such as 1-5 μM, 5-10 μM, 10-15 μM, or 15-20 μM.

In certain aspects, the media of steps (a)-(c) do not comprise or have essentially no insulin. In certain aspects, the Activin agonist is Activin A. In some aspects, the media of step (a) further comprises albumin. In certain aspects, the media of any of steps (a)-(c) further comprises albumin.

In some aspects, the PSC aggregates of step (a) were obtained by culturing PSCs in the presence of a Wnt agonist and a survival agent. In some aspects, the Wnt agonist is CHIR 99021, SB216763, CHIR 98014, TWS119, Tideglusib, SB415286, BIO, AZD2858, AZD1080, AR-A014418, TDZD-8, LY2090314, or IM-12. In particular aspects, the Wnt agonist is CHIR 99021. In some aspects, the CHIR 99021 is present in step (a) at a concentration of about 0.5 to 5 μM, such as about 1 μM to 3 μM, such as 1 μM, 2 μM, or 3 μM. In certain aspects, the survival agent is a Rho-associated kinase (ROCK) inhibitor or myosin II inhibitor. In some aspects, the ROCK inhibitor is H1152 or Y-27632. In certain aspects, the myosin II inhibitor is H1152.

In certain aspects, the mesoderm progenitor cells are dissociated into essentially single cells prior to step (c). In some aspects, the media of step (c) is free of or essentially free of BMP4, a Wnt agonist, and retinoic acid. In certain aspects, Wnt inhibitor of step (c) is XAV939, IWR1, IWR2, IWR3, IWR4, ICG-001, IWR-1-endo, Wnt-059, LGK-974, LF3, CP21R7, NCB-0846, PNU-74654, or KYA179K. In some aspects, the Wnt inhibitor is XAV939. In certain aspects, the XAV939 is present in the media at a concentration of 0.5 μM to 10 μM, such as 1 μM to 5 μM, such as 1 μM, 2 μM, 3 μM, 4 μM, or 51 μM.

In some aspects, the population of WT1+ epicardial progenitor cells in step (c) comprise at least 30% (e.g., 35%, 40%, 45%, 50%, 55%, 60%, 65%, 70%, 75%, 80%, 85%, 90%, 95%, 99% or more) positive WT1+ epicardial progenitor cells. In certain aspects, the population of WT1+ epicardial progenitor cells in step (c) comprise less than 80% (e.g., less than 85%, 90%, 95%, 98%, 99%, or 100%, such as less than 75%, 70%, 65%, 60%, 50%, or 40%) positive WT1+ epicardial progenitor cells.

In certain aspects, the method does not comprise a purification step between step (c) and differentiating the cells to cardiac fibroblasts. In some aspects, the purification step is further defined as cell sorting.

In particular aspects, the TGFβ inhibitor is SB431542, LDN-193189, LY2157299, LY2109761, SB525334, SIS HCl, SB505124, GW788388, or LY364947. In specific aspects, the TGFβ inhibitor is SB431542. In some aspects, the SB431542 is present in the media at a concentration of 1 μM to 10 μM, such as 1-5 μM, 5-10 μM, 1-3 μM, 3-7 μM, or 7-10 μM.

In certain aspects, the media of step (a) is free of or essentially free of a Wnt agonist and Wnt inhibitor. In some aspects, the media of step (b) is free of or essentially free of TGFβ inhibitor. In certain aspects, the media of step (b) further comprises serum.

In certain aspects, the bFGF is present in the media at a concentration of 50-200 ng/mL. In some aspects, the media of step (b) is free of or essentially free of serum. In particular aspects, the bFGF is present in the media at a concentration of 10-100 ng/mL. In further aspects, the media further comprises VEGF, EGF, and/or IGF.

In some aspects, the population of cardiac fibroblasts comprises at least 75% (e.g., 80%, 85%, 90%, 95%, 99%, or 100%) cells positive for TE-7, CD29, and/or CD90. In certain aspects, the population of cardiac fibroblasts comprises at least 85% cells positive for TE-7, CD29, and/or CD90.

In particular aspects, the cardiac fibroblasts are quiescent cardiac fibroblasts. In some aspects, the population of cardiac fibroblasts comprises less than 15%, 10%, or 5% (e.g., 4%, 3%, 2%, 1% or less) cells positive for alpha smooth muscle actin (αSMA). In some aspects, the population of cardiac fibroblasts comprises at least 85% cells positive for TE-7, CD90 and CD29 and less than 5% cells positive for αSMA.

In additional aspects, the method further comprises cryopreserving the population of cardiac fibroblasts.

In some aspects, the method further comprises culturing the population of cardiac fibroblasts in the presence of TGFβ to produce a population of activated cardiac fibroblasts. In some aspects, the TGFβ is present at a concentration of 10-100 ng/mL, such as 10-25, 25-50, 50-75, or 75-100 ng/mL. In some aspects, the population of activated fibroblasts exhibit increased fibronectin secretion and/or increased expression of αSMA as compared to the population of cardiac fibroblasts prior to culturing in the presence of TGFβ.

In certain aspects, the culture is performed in defined media. In particular aspects, the method is good manufacturing practice (GMP)-compliant.

A further embodiment provides a population of epicardial progenitor cells or cardiac fibroblasts produced by the method of the present embodiments and aspects thereof.

Another embodiment provides a composition comprising a population of PSC-derived cardiac fibroblasts with at least 75% (e.g., 80%, 85%, 90%, 95%, 99%, or 100%) expression of TE-7 and CD29 and less than 15%, 10%, or 5% (e.g., less than 4%, 3%, 2%, or 1%) expression of αSMA. In some aspects, the population of cardiac fibroblasts comprises at least 85% cells positive for TE-7, CD90 and/or CD29. In certain aspects, the population of cardiac fibroblasts comprises at least 85% cells positive for TE-7, CD90 and/or CD29 and less than 5% cells positive for αSMA. In some aspects, the cardiac fibroblasts are produced by the method of the present embodiments and aspects thereof. In some aspects, the population of cardiac fibroblasts is GMP-compliant. In certain aspects, the composition is a pharmaceutical composition.

A further embodiment provides a method for the treatment of a cardiac disorder in a subject comprising administering an effective amount of cardiac fibroblasts of the present embodiments or aspects thereof to a subject in need thereof. In some aspects, the cardiac fibroblasts are administered directly to the heart. In certain aspects, the administration is by using an intra-myocardial catheter. In some aspects, the cells are administered in a suspension comprising human albumin. In certain aspects, the human albumin is present in a concentration of 1% to 20%, such as 1% to 10%, such as 1-5% or 5-10%, such as 1%, 2%, 3%, 4%, 5%, 6%, 7%, 8%, 9%, or 10%. In some aspects, the human albumin is present in a concentration of 5%. In particular aspects, the subject is a human. In specific aspects, the cardiac disorder is fibrosis, myocardial infarction, cardiomyopathy, congestive heart failure, ventricular septal defect, atrial septal defect, congenital heart defect, ventricular aneurysm, a cardiac disorder which is pediatric in origin, ventricular aneurysm, or a cardiac disorder which requires ventricular reconstruction.

Another embodiment provides a co-culture comprising the cardiac fibroblasts of the present embodiments or aspects thereof, endothelial cells, and cardiomyocytes. In some aspects, the co-culture comprises about 40% (e.g., 45%, 50%, 55%, 60%, 65%, 70%, or 75%) cardiomyocytes, about 5% (e.g., 10%, 15%, 20%, 25%, or 30%) endothelial cells, and about 10% (e.g., 15%, 20%, 25%, or 30%) cardiac fibroblasts. In certain aspects, the co-culture comprises about 75% cardiomyocytes, about 30% endothelial cells, and about 30% cardiac fibroblasts. In some aspects, the co-culture comprises about 60% cardiomyocytes, about 20% endothelial cells, and about 20% cardiac fibroblasts. In certain aspects, the co-culture comprises about 75% cardiomyocytes, about 15% endothelial cells, and about 15% cardiac fibroblasts. In some aspects, the co-culture is further defined as a microtissue. In some aspects, the microtissue is in a microwell plate. In certain aspects, the microtissue is scaffold-free. In some aspects, the cardiomyocytes, endothelial cells, and cardiac fibroblasts are isogenic. In certain aspects, the co-culture exhibits inotropic response to beta-adrenergic agonist isoproterenol.

Another embodiment provides a method for screening a test compound comprising introducing the test compound to a cardiac fibroblast population of the present embodiments or aspects thereof. In some aspects, the method further comprises measuring cardiac fibroblast viability, cardiotoxicity, and/or cardiomyocyte function.

Further provided herein is a kit comprising a cardiac fibroblast population of the present embodiments or aspects thereof. In some aspects, the kit further comprises endothelial cells and/or cardiomyocytes. Also provided herein is the use of a kit of the present embodiments for disease modelling or disease screening.

Other objects, features and advantages of the present disclosure will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Schematic depicting cardiac progenitor induction using ABC method (Activin A, BMP4, and CHIR) vs. CHIR (GSK3 inhibitor CHIR99021) alone. (FIG. 2B) Activin A and BMP4 during mesoderm decreases the percentage of CXCR4+ progenitors compared to CHIR alone. For CHIR only, 7 μM of Chir99021 was added. For the ABC condition, 9 ng/mL Activin, 5 ng/mL BMP4, and 7 μM CHIR were added on Day 1 and Activin and BMP only were added on Day 2 of differentiation.

(FIG. 3A) Schematic of paths for fibroblasts progenitor induction: Single CHIR, ABC, and Double CHIR. (FIG. 3B) Dose dependence of Single CHIR Epicardial Cells. Increasing CHIR does not increase WT1 percentage of Epicardial (Wilms' tumor suppressor protein % (WT1%)) positive cells. FIG. 3C) Dose dependence of Single CHIR Epicardial Cells. Epicardial induction with single CHIR or ABC step produces a mixed population of epicardial cells and cardiomyocytes. The percentage of WT-1+ epicardial cells ranges from 30% WT-1 to 90% WT-1, and these cells are not highly proliferative. (FIG. 3D) Epicardial morphology of single CHIR treated cardiac progenitors. Single CHIR epicardial cells have a flattened cobblestone morphology and a pronounced round large nucleus (right). With the addition of Activin and BMP to CHIR, the cells retain a flattened cobblestone morphology, but clear cell-cell borders become less pronounced (center). Notably, with the secondary CHIR, proliferation of epicardial progenitors increased showing decreased cell size and (right) and more elongated morphology. (FIG. 3E) Activation potential of cardiac fibroblasts produced by Double CHIR and single CHIR method by quantitative real-time PCR. Cardiac fibroblasts were differentiated by the two methods. Cardiac fibroblasts from each method were treated with 20 ng/mL TGFβ for 4 days. Activation with TGFβ led to increased POSTN, DDR2, COL1A1, COL1A2, GJA1, and ACTA2 expression in single CHIR cardiac fibroblasts as well as control DBL CHIR epicardial derived cardiac fibroblasts. Notably, the basal level of ACTA2 expression in single CHIR protocol is lower than in the double CHIR protocol.

FIGS. 4A-4H: (FIG. 4A) Schematic depicting cardiac fibroblast induction method free of TGFβ inhibitor (as indicated by dark bar for SB43152). (FIG. 4B) Percentage of CD29 positive cells with varying concentration of basic FGF during cardiac fibroblast differentiation in serum. Basic FGF can be used for cardiac fibroblast differentiation in serum. Integrin beta-1 (ITGB1), also known as CD29, is a cell surface receptor that in humans is encoded by the ITGB1 gene. In cardiac fibroblasts differentiated by this method, increasing expression of CD29 was observed. In cardiac muscle and skeletal muscle, the integrin beta-1D isoform of CD29 is specifically expressed. (FIG. 4C) Purity of cardiac fibroblasts made from ABC progenitors in serum containing medium. Seven independent iPSC lines were differentiated to cardiac fibroblasts using ABC during mesoderm induction and cardiac fibroblast specification in serum-containing medium with high levels of basic FGF. All cardiac fibroblasts had high fibroblast purity (TE-7) and were quiescent having less than 5% alpha smooth muscle actin purity (αSMA). (FIG. 4D) Purity of cardiac fibroblasts from ABC progenitors induced to cardiac fibroblasts under serum free conditions. Cardiac fibroblasts were induced from epicardial cells by culturing in serum-free medium without TGFβ inhibitor for 5 passages. Resulting TE-7 and a-SMA purity of cardiac fibroblasts is shown. Cardiac fibroblasts induced in serum free medium have high TE-7 purity (>85%) and are quiescent (αSMA <5%). A volcano plot comparison of gene expression of cardiac fibroblasts produced from both methods is provided on the right. (FIG. 4E) iPSC cardiac fibroblasts activated with TGFβ. Fibronectin secretion is given as ug/mL per $\times 10^6$ cells. iPSC derived cardiac fibroblasts were plated on VTN coated plates at 10 k/$cm^2$. TGFβ was added at indicated concentration to activate cardiac fibroblasts on Day 2, with a media change on Day 4. On Day 5, media supernatants were collected and analyzed for fibronectin secretion by a Human FN ELISA Kit Cat #BMS2028. On Day 3 and Day 5, cardiac fibroblasts were harvested and counted by ViCellXR. Fibronectin secretion is given as ug/mL per $\times 10^6$ cells. After 5 days cells were collected for flow cytometry. An alpha smooth muscle actin population emerges in the presence of TGFβ (right). (FIG. 4F) Gene expression of iPSC cardiac fibroblasts by quantitative real-time PCR (qRT-PCR). iPSC cardiac fibroblasts express more GATA4, TBX20, NkX2-5, TBX18, and TCF21 than primary dermal fibroblasts. iPSC cardiac fibroblasts express collagens and connexin-43 at similar levels to primary cardiac fibroblasts. Two lots of iPSC-CF shown and compared to primary human cardiac fibroblasts, primary human dermal fibroblasts, and primary human smooth muscle cells as controls. Notably, activation related genes αSMA (ACTA2), POSTN, and GJA1 expression is lower in iPSC-CF compared to primary hCF. (FIG. 4G) Heat map of bulk RNAseq data comparing iPSC-CF (iCFB) lots with published datasets from adult primary cardiac fibroblasts (aCF), fetal primary cardiac fibroblasts (fCF), and iPSC derived cardiomyocytes for characteristic genes. (FIG. 4H) Population distribution of expression of various genes in iPSC derived cardiac fibroblasts by single cell RNA sequencing. Nearly all iPSC-CF express characteristic fibroblast markers (VIM, FN1, COL1A1, SPARC). Within the pure TE-7 population, there are sub-populations of CF expressing various lineage transcription factors including TBX3, TWIST1, GATA4, TIE-2 (TEK), SNA1I, and WT1. Only 2% of cells express canonical epicardial marker Tcf21.

(FIG. 5A) Schematic of cardiac tri-culture microtissue assay. Cryopreserved iPSC derived cell types are combined in a specific ratio and formed into microtissues in microwell plates. Microtissues are fed a co-culture medium to support all three cell types. Fourteen days post assembly, microtissues respond to challenge with inotropic compounds. (FIG. 5B) 10× phase contrast images of microtissues with a total of 5,000 cells collected on an Incucyte S3 in S-bio plates over time. (FIGS. 5C-5D) Diameter of tri-culture microtissues was quantified and compared between microtissues from different cell numbers at DIV 14. (FIG. 5E) Tri-culture cardiac microtissue on DIV14 with 10,000 total cells with 15% IPSC derived cardiac fibroblasts labelled with viability dye Acridine orange to label viable cells green.

(FIG. 6A) Isogenic tri-culture cardiac microtissues exhibit inotropic response to positive inotrope and beta-adrenergic agonist isoproterenol across iPSC-derived cardiac fibroblast clones, lot of cardiac fibroblasts, and donor lines. This response was in tri-culture microtissues from all three donor lines, in two independently produced lots of cardiac fibroblasts, and in microtissues containing cardiac fibroblasts from two independently derived clones. (FIG. 6B) Increasing inotropic response with increasing percentage of cardiac fibroblasts in tri-culture microtissues. Response to dobutamine (DOB), digoxin (DIG), isoproterenol (ISO), and epinephrine (EPI) were assessed at DIV 14 on cardiac tri-culture microtissues comprised of 10,000 total cells and 20% iPSC-derived endothelial cells and iPSC-derived cardiomyocytes and varying concentrations of iPSC-derived cardiac fibroblasts (CF). Increased CF content in cardiac 3D microtissues led to increased calcium amplitude inotropic response to dobutamine, digoxin, and epinephrine.

(FIG. 8A) Isogenic cardiac microtissues prepared from pluripotent stem cell derived cardiomyocytes, cardiac fibroblasts, and endothelial cells carrying a mutation in the lamin (LMNA) gene reveal that non-cardiomyocyte cells display disease phenotype characteristics and contribute to cardiomyocyte phenotype in vitro. Tri-culture microtissues were made from Normal Healthy Control (NHC) and isogenic LMNA-L35P iPSC derived cell types as previously described. Fourteen days post microtissue formation, microtissues were challenged with isoproterenol. Microtissues from normal healthy donor iPSC responded with an increase in calcium transient amplitude at 100 nM isoproterenol. The disease model microtissue did not respond to increased isoproterenol Immunofluorescence of LMNAL35P iPSC derived cardiomyocytes shows deformed nuclear lamina as predicted by genotype. (FIG. 8B) An in vitro model, such as a cardiac tri-culture microtissue can also be used to understand the impact of environmental stressors on genetic cardiovascular diseases. A striking impact of hypoxia was observed on the beat rate of isogenic LMNA 135P microtissues. Tri-culture microtissues were made from Normal Healthy Control (NHC); isogenic LMNA corrected, and isogenic LMNA-L35P iPSC derived cell types. After cells were beating, cells were placed in hypoxia (5% 02) or normoxia (20% 02). (Left) Normal healthy control microtissue, and isogenic LMNA mutation corrected microtissues had similar beat rates in normoxia and hypoxia while LMNA mutant tri-culture MT had significantly slower beat rate in hypoxia. (Right) Example DIV14 Ca2+ transients.

DESCRIPTION OF ILLUSTRATIVE EMBODIMENTS

Figure 1:
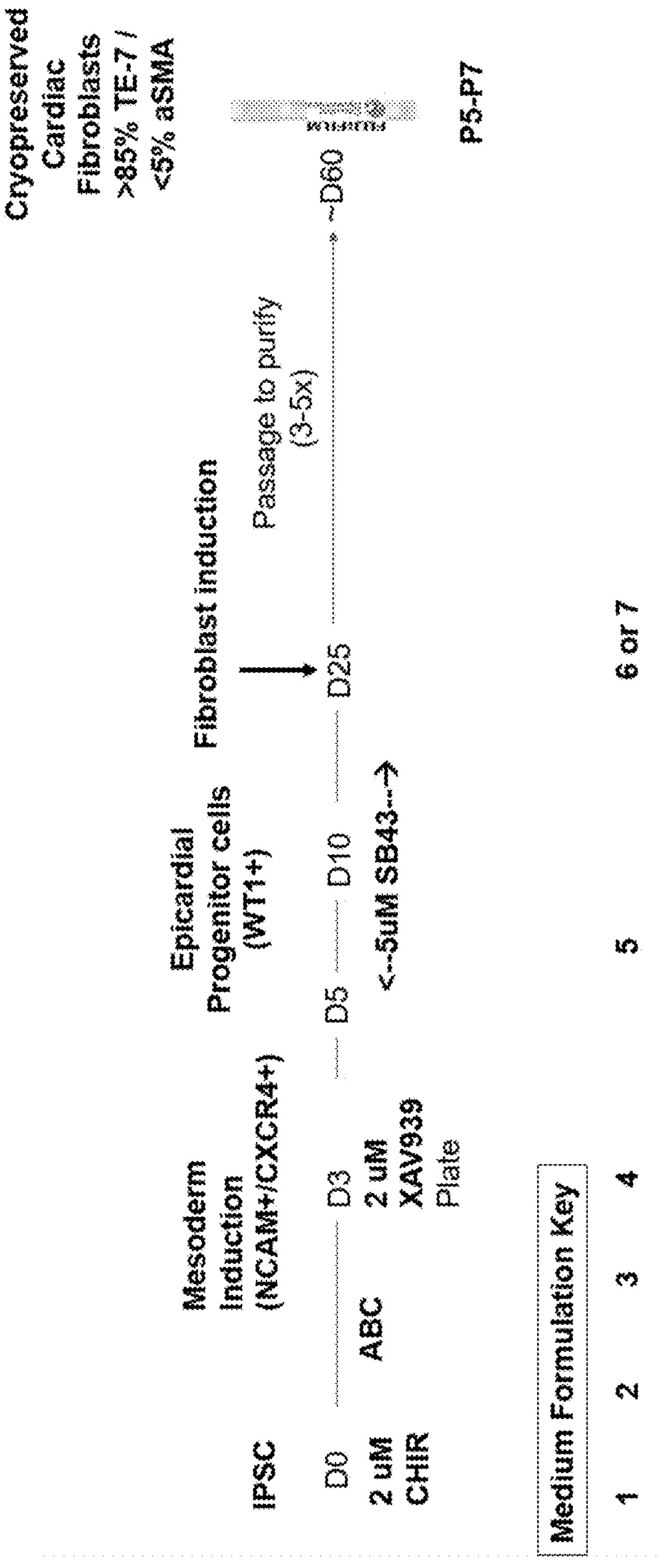
FIG. 1: Schematic depicting cardiac fibroblast protocol.

In certain embodiments, the present disclosure provides methods for generating highly pure populations of cryopreserved quiescent cardiac fibroblasts from a population of WT1+ cardiac progenitor cells, such as epicardial cells, by the addition of serum-containing medium or non-serum containing medium in the presence of basic FGF (FIG. 1). Further provided herein are methods of generating a mixed population of cardiomyocytes and WT1+ cardiac progenitor cells, such as epicardial cells. In some aspects, the cardiac progenitor cells are oligopotent and can differentiate to multiple types of cardiac cells.

In some aspects, the starting population of iPSCs can be cultured in either hypoxic or normoxic conditions prior to differentiation to cardiac fibroblasts. To differentiate iPSCs to cardiac progenitor cells, the starting iPSCs can be formed into aggregates in a low concentration of GSK3 inhibitor in E8 medium comprising ROCK inhibitor. To initiate differentiation, on Day 1, iPSCs may be treated with a high level GSK3 inhibitor for one day and in the presence of Activin A and Bone Morphogenetic Protein 4 (BMP4) growth factors. Activin A and BMP4 treatment is continued for an additional day for a total of two days.

Figure 2A:
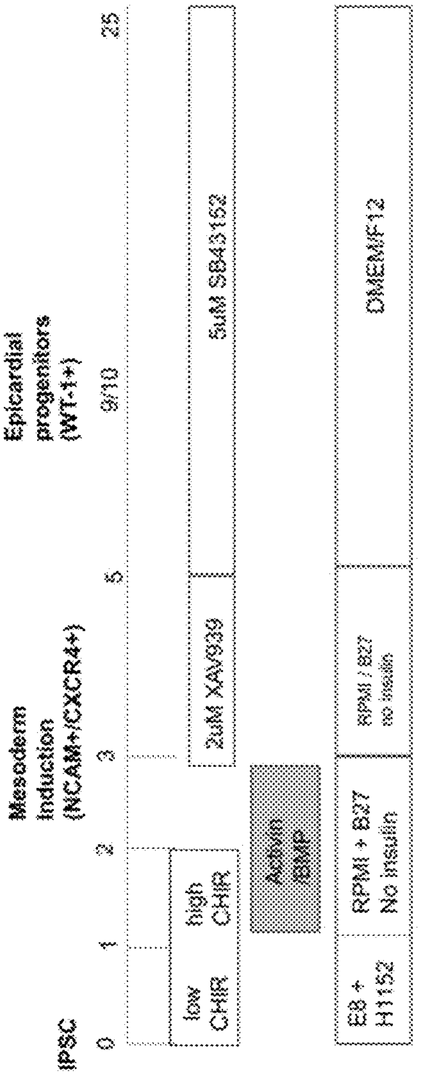
FIGS. 2A-2B.
Figure 2B:
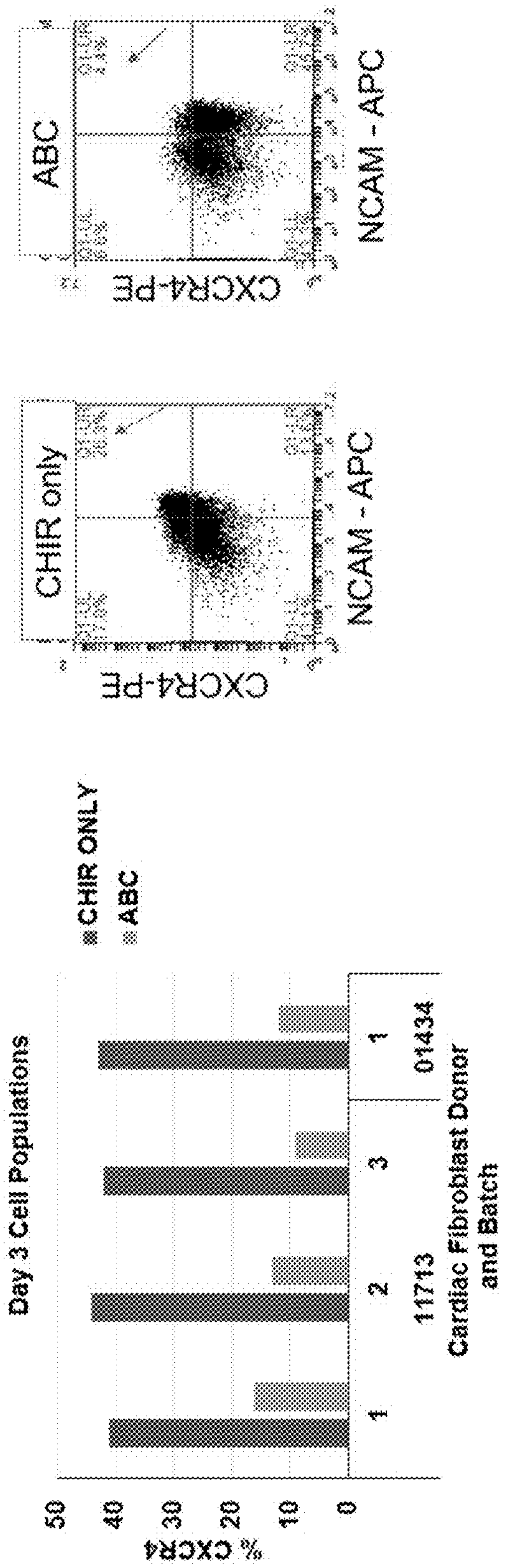

In the present studies, with the addition of activin and BMP4 (ABC, FIG. 2A) to the mesoderm induction medium, a decrease was observed in the composition of the cardiac progenitor marker CXCR4 compared to GSK3 inhibition alone (FIG. 2B). On Day 3, cardiac progenitors were plated and treated with a low level of Wnt inhibitor. On Day 5, no additional Wnt modulation was performed (FIG. 3A) and a mixture of epicardial cells and cardiomyocytes was produced (FIG. 3B). A TGFβ inhibitor was then added to support epicardial cells. Notably, without a secondary GSK3 inhibition, proliferation of epicardial progenitors was found to be decreased (FIG. 3C). By Day 10, a mixed population of epicardial progenitors (WT1+) and cardiomyocytes (cTNT+) was produced. During extended culture of epicardial progenitors from Day 10 to Day 25, the cardiomyocyte population decreased and was subsequently eliminated following cardiac fibroblast induction and passaging.

In some aspects, the present methods comprise an assembloid approach in which three separate differentiations are used to generate three separate pure population of cells and then combined. The assembloid approach allows for precisely controlled and reproducible control of cell compositions. Alternatively, an organoid approach may be used in which co-differentiation of different cells types is performed, such as a mixed population of cardiomyocytes and epicardial cells is produced.

Figure 4A:
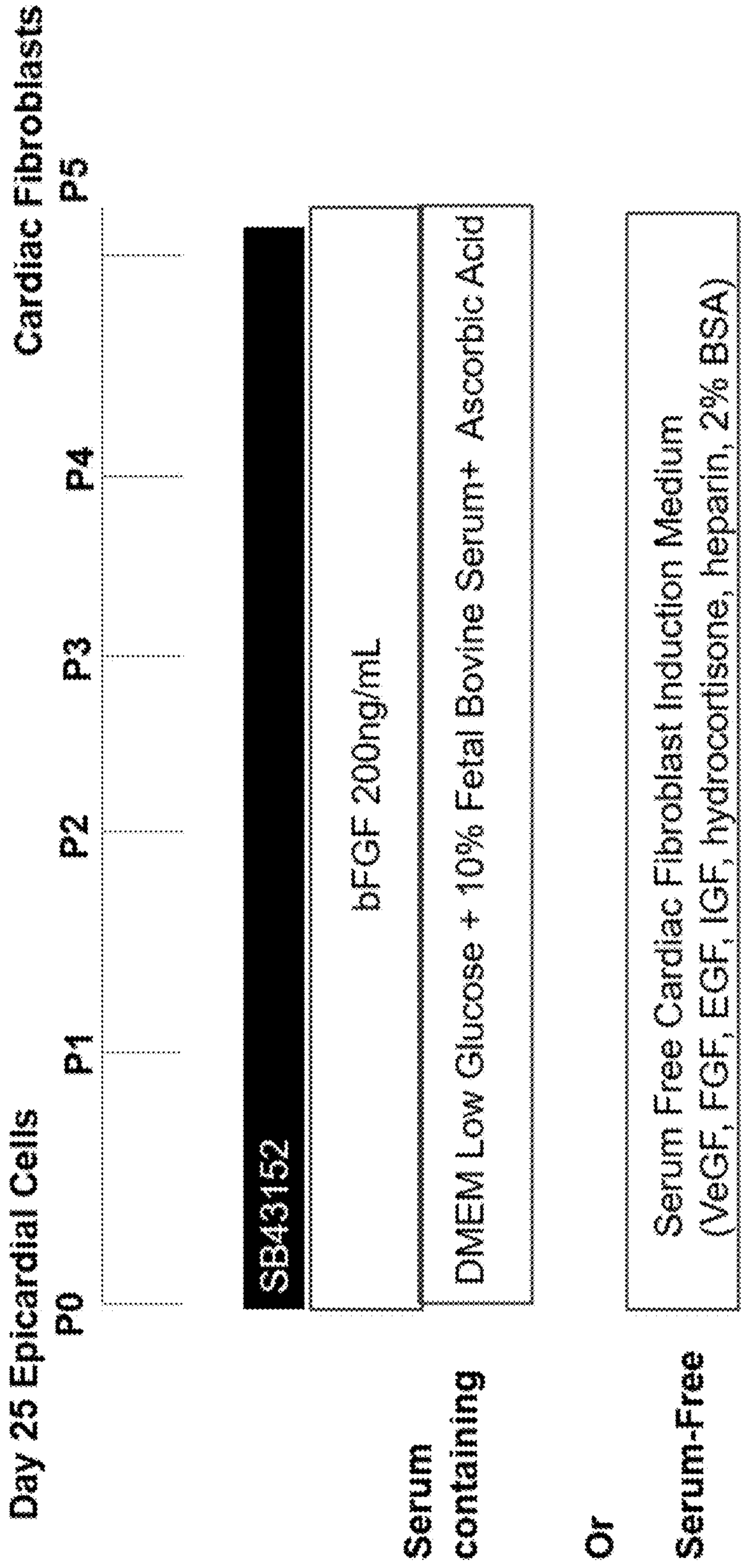
Figure 4B:
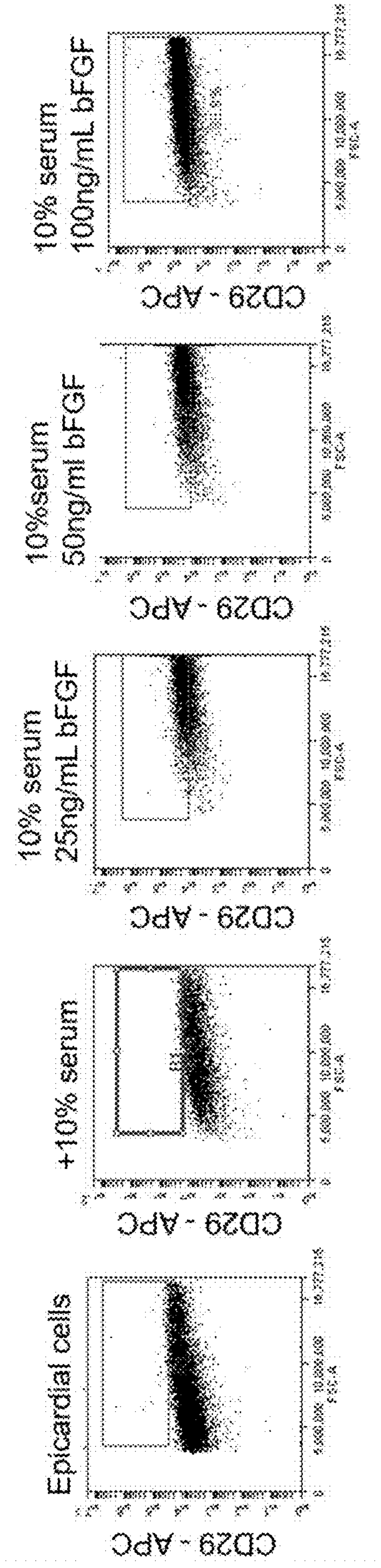
Figure 4C:
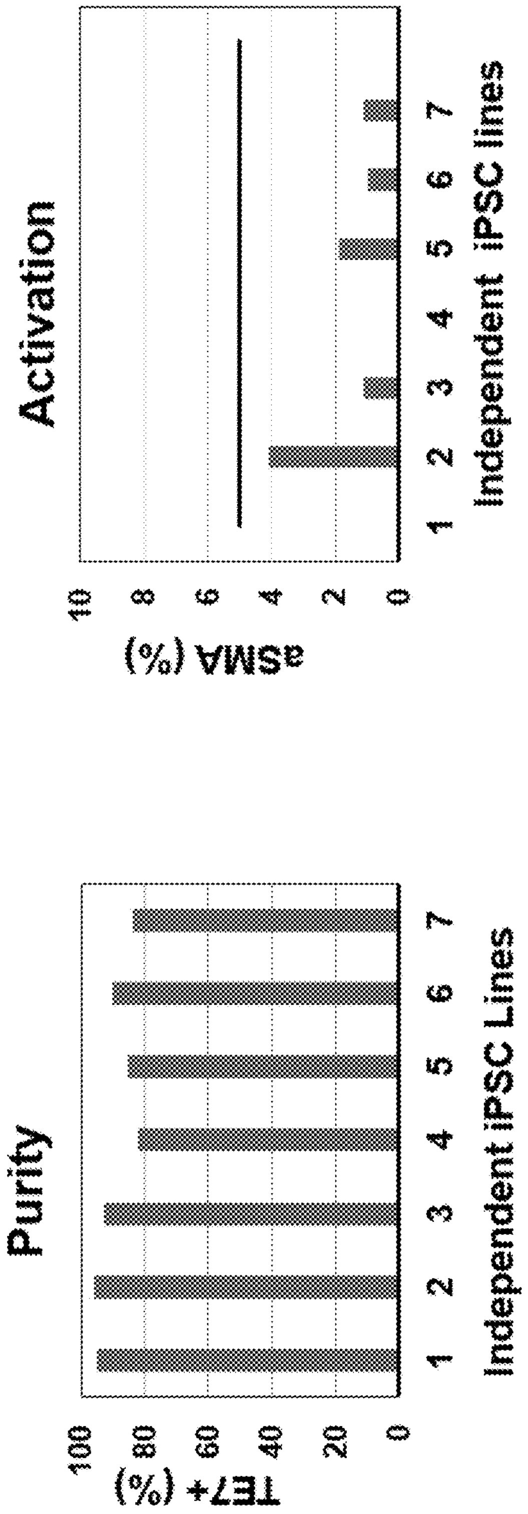

Two methods were developed for cardiac fibroblast induction (FIG. 4A). Cardiac fibroblast induction was initiated by removing the TGFβ inhibitor. For serum containing cardiac fibroblast induction, Day 25 epicardial cells were transitioned to DMEM-low glucose medium, 10% serum, with ascorbic acid and basic FGF. Cardiac fibroblasts were passaged when reaching 80% confluency and attained more than 75% TE-7 purity within P3-P5. Increasing cardiac fibroblast purity by TE-7 and CD-29 was observed with increasing basic FGF (FIG. 4B). These cardiac fibroblasts were quiescent (e.g., less than <5% αSMA,) and expressed genes and proteins characteristic of cardiac fibroblasts (FIG. 4C).

Figure 4D:
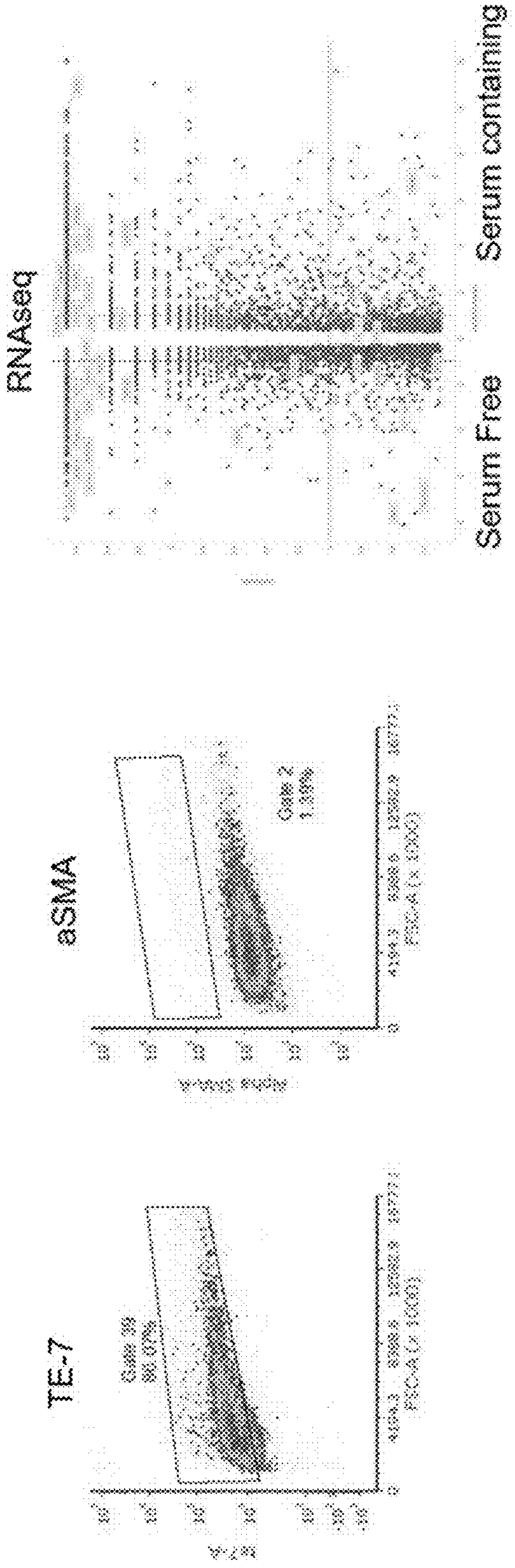
Figure 4E:
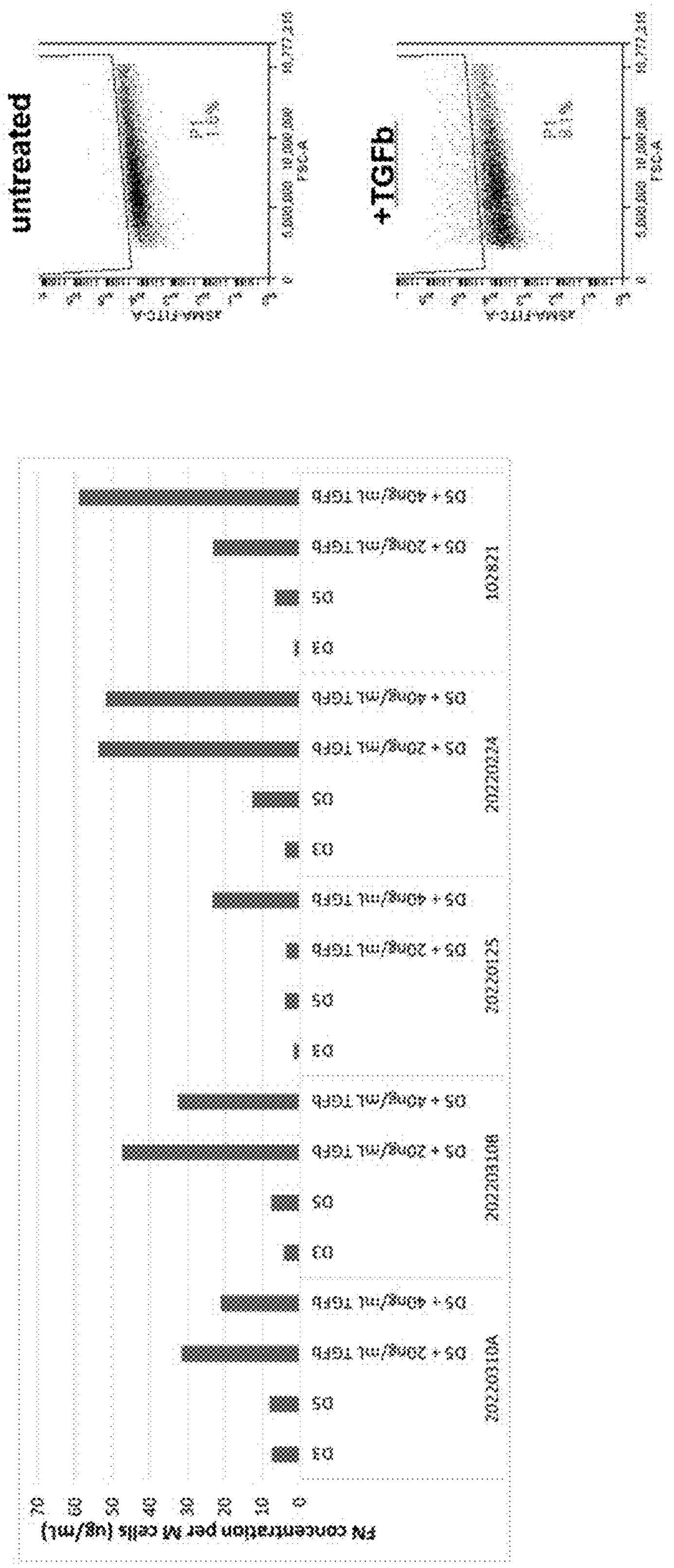
Figure 4F:
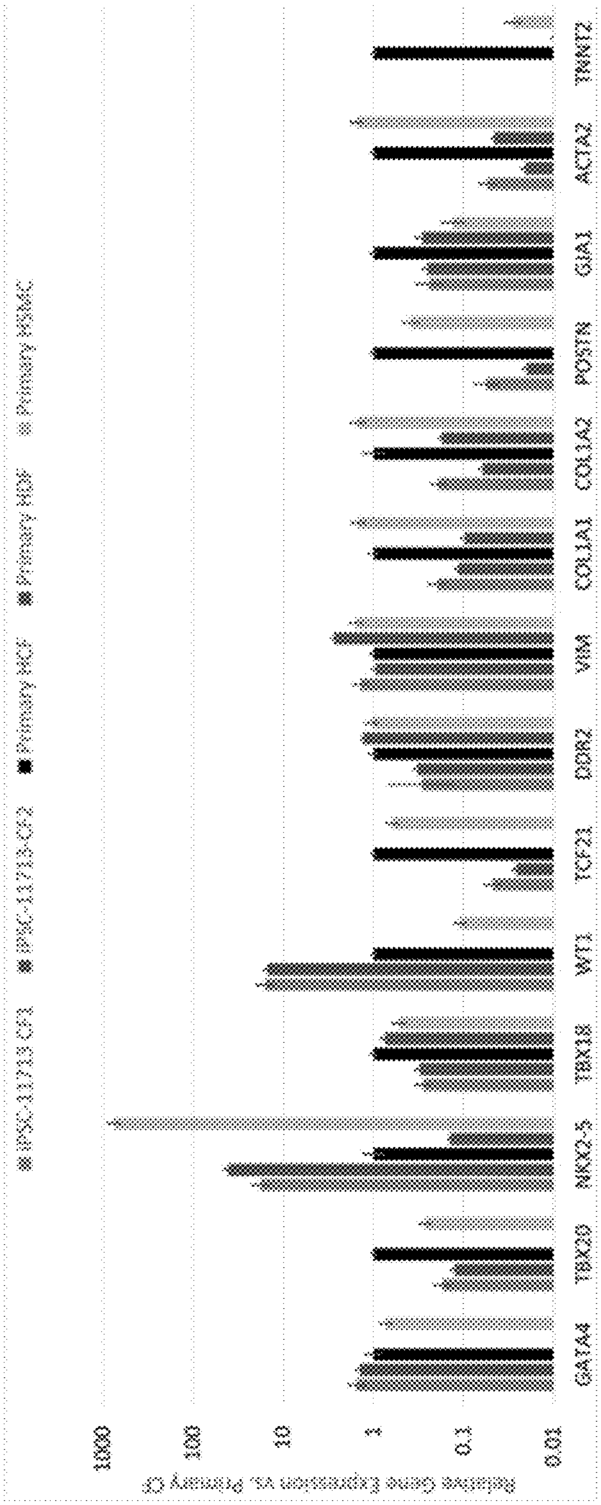
Figure 4G:
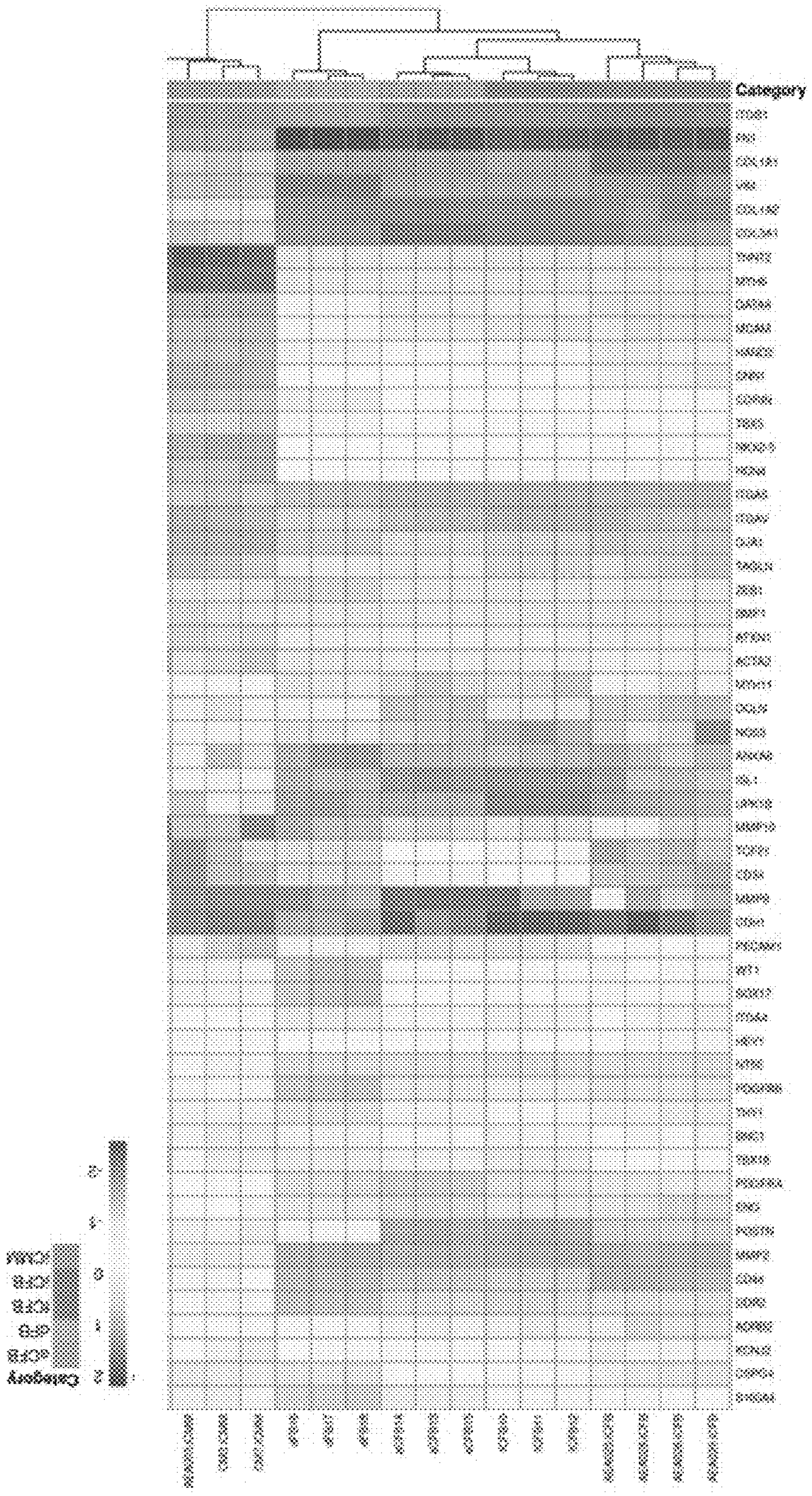

For cardiac therapeutic applications, an alternative serum-free cardiac fibroblast induction protocol was also developed. In some aspects, epicardial cells were induced to cardiac fibroblasts by culture in serum-free medium containing VEGF, EGF, FGF, and/or IGF starting as early as Day 17. In some aspects, the medium does not comprise VEGF. Within 5 passages, a pure population of quiescent cardiac fibroblasts (e.g., 85% TE-7, and less than 5% αSMA) was achieved with similar gene expression profiles (FIG. 4D). Cardiac fibroblasts from serum-containing and serum-free were activated with treatment with TGFβ and increased fibronectin secretion and alpha smooth muscle actin expression was observed (FIG. 4E). Cardiac fibroblasts were cryopreserved between P5-P15 and used for microtissue assay.

Accordingly, further provided herein is an isogenic microtissue composition assembled from PSC-derived cryopreserved, purified cell populations including cardiomyocytes, cardiac fibroblasts, and endothelial cells that exhibit "mature" inotropic responses.

Figure 5A:
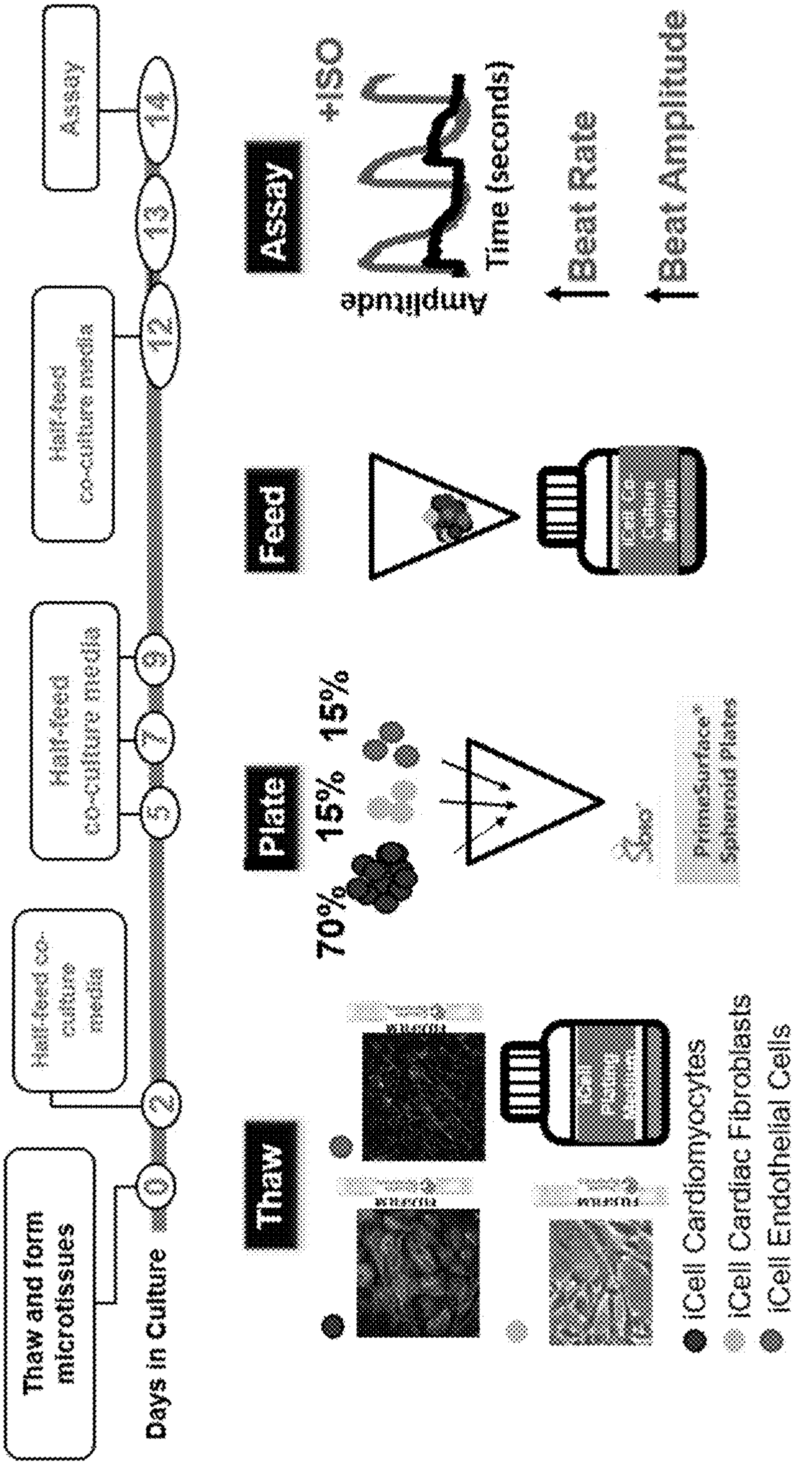
FIGS. 5A-5E.
Figure 5B:
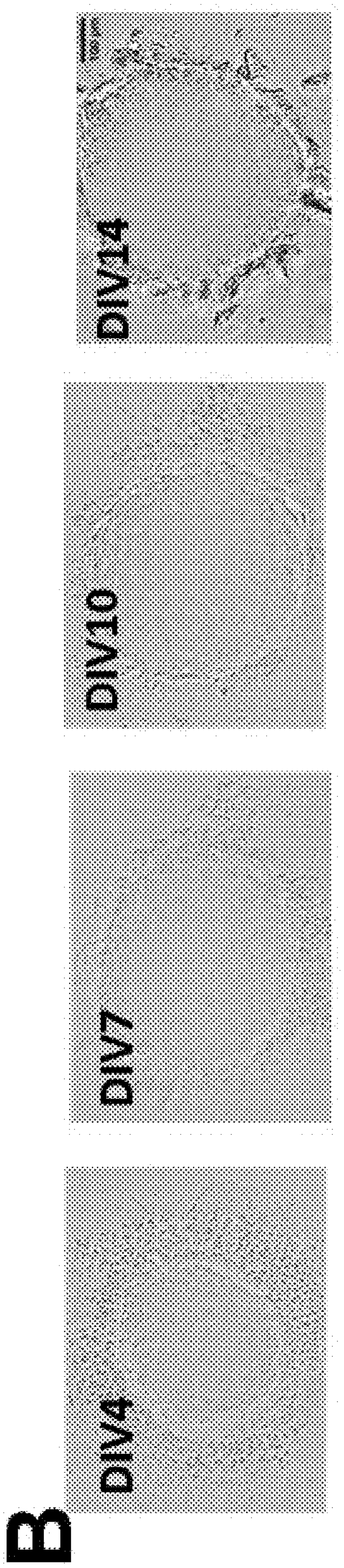
Figure 5C:
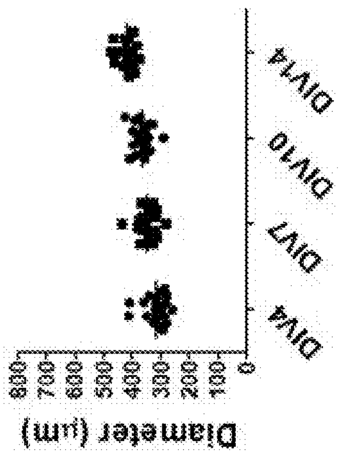
Figure 5D:
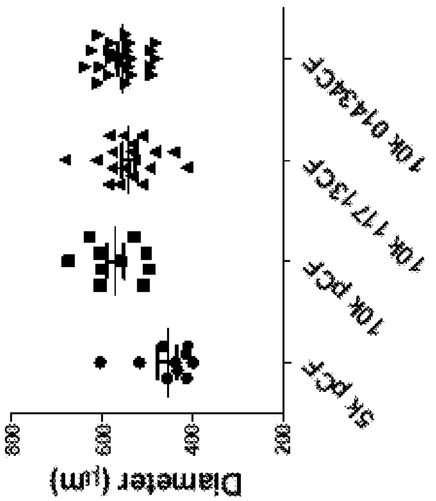
Figure 5E:
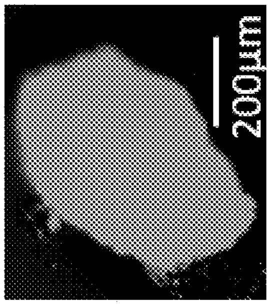

Isogenic tri-culture microtissues may be formed from cryopreserved cardiomyocytes, endothelial cells, and cardiac fibroblasts derived from apparently healthy normal isogenic iPSC (FIG. 5A). Tri-culture isogenic microtissues can be formed with 500-20,000 total cells (FIG. 5B). Half-media exchanges may be performed every other day and culture continued for 14-21 days in co-culture medium (Table 8). Microtissues spontaneously contract within 2-4 days. A microtissue formed with 5,000 total cells can increase in size from an average diameter of 300-450 μm over 14 days. Microtissues may be assayed for response to isoproterenol after fourteen days in co-culture.

Figure 6A:
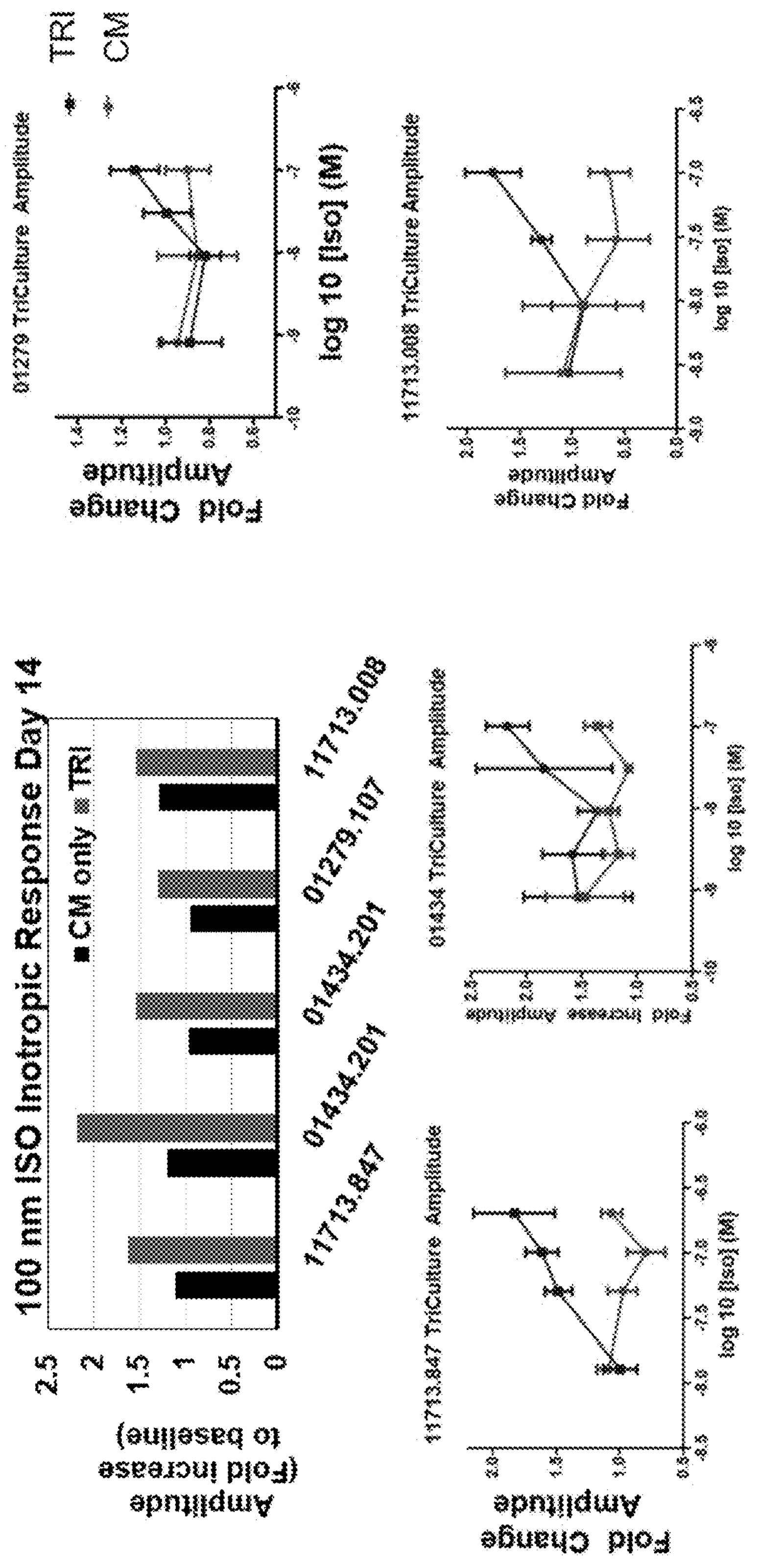
FIGS. 6A-6B.
Figure 6B:
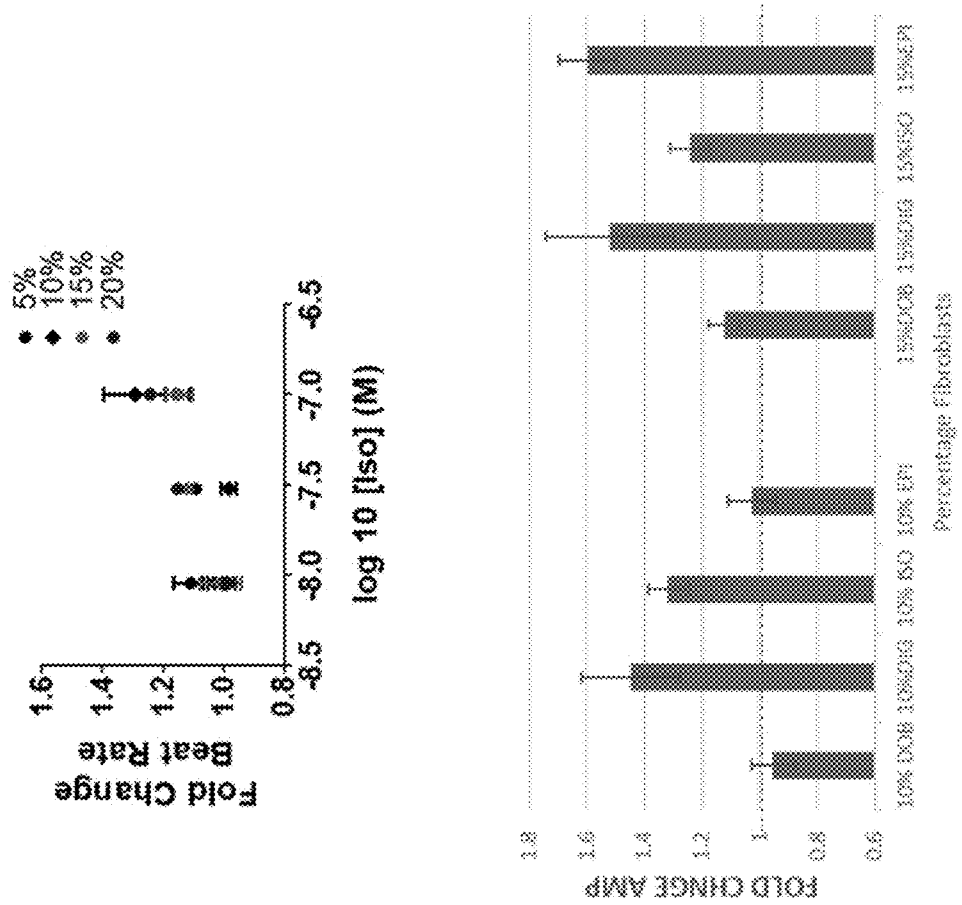

In the present studies, unlike microtissues from only PSC-derived cardiomyocytes, isogenic tri-culture microtissues demonstrated both an increase in beat rate and beat amplitude (inotropic response, FIG. 6A) by calcium transient in the presence of isoproterenol. The magnitude of the inotropic response increased with increasing the percentage of cardiac fibroblasts incorporated into the microtissue (FIG. 6B).

Figure 7:
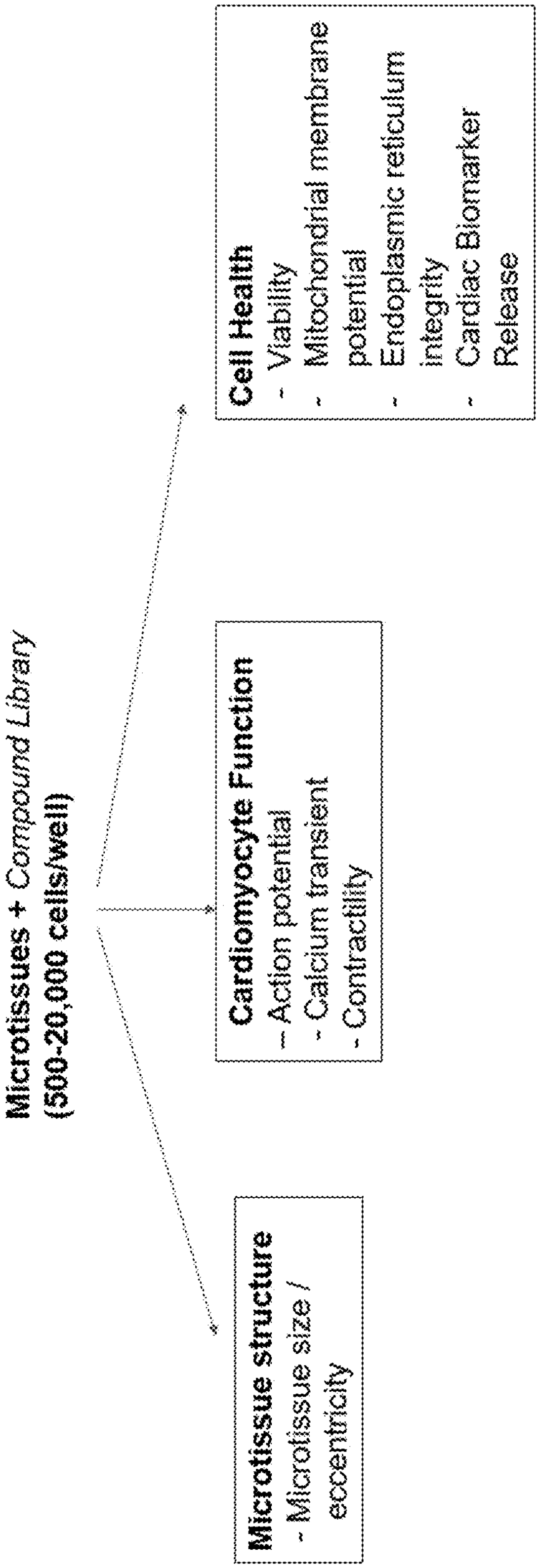
FIG. 7: Compound library screening with cardiac tri-culture microtissues derived from isogenic cell types. Cardiac tri-culture microtissue are highly amenable to high-throughput screening for cardiovascular drug discovery. Small numbers of cells can be used in multiwell plates (e.g., 96, 384, 1536) across numerous high-throughput assay platforms.

Further provided herein is a screening kit comprising the present PSC-derived cardiac fibroblasts and microtissue for cardiotoxicity screening. The kit can contain all three cell types derived from an iPSC from an apparently healthy donor used to screen a compound library (FIG. 7A).

Also provided herein is a kit for isogenic disease modelling or screening for rare diseases comprising the present PSC-derived cardiac fibroblasts and microtissue. The kit may contain all three cell types derived from an iPSC with a genetic disease genotype or derived from iPSC engineered with a disease-relevant mutation (FIG. 7B).

Further embodiments provide methods for the application of cardiac tri-culture assay containing three stem cell derived cell types cardiomyocytes, endothelial cells, and fibroblasts for in vitro disease modelling, drug discovery, and toxicity testing.

In addition, the present disclosure provides therapies comprising administering the cardiac fibroblasts cells or materials derived from cardiac fibroblasts (i.e. matrix, vesicles, and/or secreted factors) provided herein. The cells may be delivered by direct injection or by trans-endocardial, intra-myocardial catheter delivery, as part of a cardiomyocyte and cardiac fibroblast patch. The cardiac fibroblast cells of the present disclosure may be manufactured from HLA-compatible iPSC for compatibility with subjects to be treated. The current methods may be used for cGMP manufacturing, including the use of all described materials and culture formats. Thus, the present disclosure provides a robust, reproducible, and relevant source of cells, such as to advance drug development and cardiac regenerative medicine.

II. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPScs or iPS cells".

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPScs or iPS cells)" are cells generated by reprogramming a somatic cell by expressing or inducing expression of a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, Oct4 (sometimes referred to as Oct3/4), Sox2, c-Myc, Klf4, Nanog, and Lin28. In some embodiments, somatic cells are reprogrammed by expressing at least two reprogramming factors, at least three reprogramming factors, at least four reprogramming factors, at least five reprogramming factors, at least six reprogramming factors, or at least seven reprogramming factors to reprogram a somatic cell to a pluripotent stem cell.

"Pluripotent stem cell" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system).

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

"Programming" is a process that alters the type of progeny a cell can produce. For example, a cell has been programmed when it has been altered so that it can form progeny of at least one new cell type, either in culture or in vivo, as compared to what it would have been able to form under the same conditions without programming. This means that after sufficient proliferation, a measurable proportion of progeny having phenotypic characteristics of the new cell type are observed, if essentially no such progeny could form before programming; alternatively, the proportion having characteristics of the new cell type is measurably more than before programming. This process includes differentiation, dedifferentiation and transdifferentiation.

"Reprogramming" is a process that confers on a cell a measurably increased capacity to form progeny of at least one new cell type, either in culture or in vivo, then it would have under the same conditions without reprogramming More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming.

"Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Typically, transdifferentiation by programming occurs without the cells passing through an intermediate pluripotency stage—i.e., the cells are programmed directly from one differentiated cell type to another differentiated cell type.

Under certain conditions, the proportion of progeny with characteristics of the new cell type may be at least about 1%, 5%, 25% or more in order of increasing preference.

The term "forward programming" refers to the programming of a multipotent or pluripotent cell, as opposed to a differentiated somatic cell that has no pluripotency, by the provision of one or more specific lineage-determining genes or gene products to the multipotent or pluripotent cell. For example, forward programming may describe the process of programming ESCs or iPSCs to hematopoietic precursor cells or other precursor cells, or to hematopoietic cells or other differentiated somatic cells.

As used herein, the term "subject" or "subject in need thereof" refers to a mammal, preferably a human being, male or female at any age that is in need of a cell or tissue transplantation. Typically, the subject is in need of cell or tissue transplantation (also referred to herein as recipient) due to a disorder or a pathological or undesired condition, state, or syndrome, or a physical, morphological or physiological abnormality which is amenable to treatment via cell or tissue transplantation.

A "survival agent" refers to an agent which promotes and/or supports cell survival when added to cell culture media. For example, Rho-associated kinase (ROCK) inhibitors or Myosin II-specific inhibitors may be used as survival agents. In particular aspects, these survival agents promote aggregation of cells in culture.

"Rho-associated kinase inhibitors," abbreviated as "ROCK inhibitors," refer to any substance that inhibits or reduces the function of Rho-associated kinase or its signaling pathway in a cell, such as a small molecule, an siRNA, a miRNA, an antisense RNA, or the like. "ROCK signaling pathway," as used herein, may include any signal processors involved in the ROCK-related signaling pathway, such as the Rho-ROCK-Myosin II signaling pathway, its upstream signaling pathway, or its downstream signaling pathway in a cell. Examples of ROCK inhibitors include, but are not limited to, a Rho-specific inhibitor, a ROCK-specific inhibitor, a MRLC (myosin regulatory light chain)-specific inhibitor, or a Myosin II-specific inhibitor.

"Cardiac fibroblasts" refer to fibroblasts in the heart that play an important role in cardiac development, contractility of the heart, and response to disease. There are no unique markers for cardiac fibroblasts; they express a combination of fibroblast associated and cardiac associated genes. Cardiac fibroblasts are responsible for generating and organizing the extracellular matrix by secreting proteins such as Collagen (Col1 A1) and Fibronectin (FN1), Periostin (POSTN), and ECM regulatory proteins matrix metalloproteases (MMPs) and their inhibitors, tissue inhibitors of metalloproteinases (TIMPs). The extracellular matrix produced by the cardiac fibroblasts serves to organize and support the myocytes of the heart during development. Cardiac fibroblasts also secrete cytokines including Interleukin-6 (IL-6), transforming growth factor beta (TGF-B), and growth factors such as connective tissue growth factor (CTGF) in response to injury or disease. Cardiac fibroblasts can be derived from several developmental lineages characterized by expression of distinct transcription factors including cardiac progenitor (TBX20+ GATA4+), epicardial (WT1+, TBX18+. TCF21+), neural crest (PAX3+), and endothelial (TIE2+).

"Stem cell-derived cardiac fibroblasts" refer to a cell whose differentiation has been manipulated towards a cardiac fibroblast like fate. Stem cell-derived cardiac fibroblasts may express markers characteristic of fibroblasts including extracellular matrix proteins including collagen I, collagen III, fibronectin, and matrix metalloproteases (MMP2, MMP14). Cardiac fibroblasts can also express transcription factors reflecting their developmental origin. Importantly, cardiac fibroblasts can express a wide variety of ion channels including potassium and transient receptor potential (TRP) channels that enable electrical and calcium coupling with cardiomyocytes. They also express connexins such as connexin 43 (GJA1) that enable them to electrically couple with cardiomyocytes.

"Epicardial progenitors" refer to multipotent progenitors in the outer layer of the heart that give rise to cardiac fibroblasts, smooth muscle, and endothelial lineages. Pluripotent stem cell derived epicardial progenitors are derived from cardiac progenitor cells. Epicardial progenitors can be cryopreserved. When plated in FGF containing medium these cells will preferentially differentiate to cardiac fibroblasts that express TE-7, CD29, and CD90. Exemplary epicardial progenitor cell markers include WT-1, TBX18, Tcf21, ALDH1A1, KRT8, KRT19, BNC1, UPK3B, ANAXA8, TJP1, and IGFBP6.

"Cardiomyocytes" or cardiac muscle cells refer to myocytes that make up the cardiac muscle. Examples of cardiac specific markers include α-sarcomeric actinin, troponin, myosin heavy chain, or L-type calcium current.

"Quiescent fibroblasts" as used herein are characterized by the low expression of α-smooth muscle actin (αSMA) whereas activated myofibroblasts express high levels of α-smooth muscle actin (αSMA). Myofibroblasts demonstrate a contractile phenotype and have increased ability to produce ECM. In some aspects, quiescent cardiac fibroblasts are fibroblasts that remain in a biologically relevant unactivated state. They can secrete extracellular matrix and can be transitioned to an activated myo-fibroblast state upon injury or exposure to a pro-fibrotic stimulus (e.g., TGFβ).

As used herein, "administering" shall mean delivering in a manner which is affected or performed using any of the various methods and delivery systems known to those skilled in the art. Administering can be performed, for example, intravenously, orally, via implant, transmucosally, transdermally, intramuscularly, or subcutaneously. Specifically, envisioned is topical administration. "Administering" can also be performed, for example, once, a plurality of times, and/or over one or more extended periods.

"Super donors" are referred to herein as individuals that are homozygous for certain MHC class I and II genes. These homozygous individuals can serve as super donors and their cells, including tissues and other materials comprising their cells, can be transplanted in individuals that are either homozygous or heterozygous for that haplotype. The super donor can be homozygous for the HLA-A, HLA-B, HLA-C, HLA-DR, HLA-DP or HLA-DQ locus/loci alleles, respectively.

A "mature" inotropic response is used interchangeably with a "physiologically" relevant inotropic response and inotropic response. Previous iPSC cardiomyocytes in 2D culture under standard conditions showed an immature or incorrect response to inotropes. When challenged with a positive inotropic compound (e.g. isoproterenol, dobutamine), cardiomyocytes increase both the contraction frequency and contraction strength, similar to adult human cardiomyocytes. In the present embodiments, by forming a microtissue containing cardiomyocytes, endothelial cells, and cardiac fibroblasts and culturing for 14 days, there is an increase in cardiomyocyte calcium transient amplitude not observed in 2D or a microtissue containing only cardiomyocytes.

An "assembloid" refers to a spheroid comprised of pre-differentiated purified cell types in contrast to an organoid where pluripotent stem cell lineages are co-differentiated together under conditions permissive to multiple cell types. In an assembloid, developmental state and composition of the cell types is precisely controlled.

"Willems tumor 1+(WT1+)" is a characteristic marker of pro-epicardial cell lineage. Epicardial progenitor cells expresses WT1. WT-1+ is also expressed in the myocardial layer and has been found in the cardiac endothelial cells of small capillaries and larger coronary vessels in mice and human during development.

The term ($CXCR4^{low}$ or CXCR4 low positive) as used herein refers to the population of cells being less than 10% (e.g., less than 9%, 8%, 7%, 6%, or 5%) positive for CXCR4. In addition, the cells can have a low signal intensity as measured by flow cytometry.

III. Pluripotent Stem Cells

In certain embodiments of the present disclosure, there are disclosed methods and compositions for providing epicardial progenitors and cardiac fibroblasts from pluripotent stem cells. The pluripotent stem cells may be stem cells including but are not limited to, induced pluripotent stem cells and embryonic stem cells.

In particular aspects, the pluripotent stem cells used herein are human embryonic stem cells (ESCs) or induced pluripotent stem cells (iPSCs) which are capable of long-term proliferation in vitro, while retaining the potential to differentiate into all cell types of the body, including the cardiac progenitor cells of the present disclosure. Thus, these cells could potentially provide an unlimited supply of patient-specific functional cardiac progenitor cells for both drug development and therapeutic uses.

A. Embryonic Stem Cells

In certain aspects, the pluripotent stem cells are embryonic stem cells (ESCs). ES cells are derived from the inner cell mass of blastocysts and have a high in vitro differentiating capability. ES cells can be isolated by removing the outer trophectoderm layer of a developing embryo, then culturing the inner mass cells on a feeder layer of non-growing cells. The replated cells can continue to proliferate and produce new colonies of ES cells which can be removed, dissociated, replated again and allowed to grow. This process of "subculturing" undifferentiated ES cells can be repeated a number of times to produce cell lines containing undifferentiated ES cells (U.S. Pat. Nos. 5,843,780; 6,200,806; 7,029,913). ES cells have the potential to proliferate while maintaining their pluripotency. For example, ES cells are useful in research on cells and on genes which control cell differentiation. The pluripotency of ES cells combined with genetic manipulation and selection can be used for gene analysis studies in vivo via the generation of transgenic, chimeric, and knockout mice.

Methods for producing mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be produced or derived from a zygote or blastocyst-staged mammalian embryo produced by the fusion of a sperm and egg cell, nuclear transfer, pathogenesis, or the reprogramming of chromatin and subsequent incorporation of the reprogrammed chromatin into a plasma membrane to produce an embryonic cell by previously described methods (Thomson and Marshall, 1998; Reubinoff et al., 2000). In one method, human blastocysts are exposed to anti-human serum, and trophectoderm cells are lysed and removed from the inner cell mass which is cultured on a feeder layer of mouse embryonic fibroblasts. Further, clumps of cells derived from the inner cell mass are chemically or mechanically dissociated, replated, and colonies with undifferentiated morphology are selected by micropipette, dissociated, and replated. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as MATRIGEL™ or laminin in the presence of "conditioned" medium containing basic fibroblast growth factor (Xu et al., 2001).

ES cells can also be derived from other organisms including rhesus monkey and marmoset by previously described methods (Thomson and Marshall, 1998; Thomson et al., 1995; Thomson and Odorico, 2000; U.S. Pat. No. 5,843,780), as well as from established mouse and human cell lines. For example, established human ES cell lines include MAOI, MA09, ACT-4, HI, H7, H9, H13, H14 and ACT30. As a further example, mouse ES cell lines that have been established include the CGR8 cell line established from the inner cell mass of the mouse strain 129 embryos, and cultures of CGR8 cells can be grown in the presence of LIF without feeder layers.

ES stem cells can be detected by protein markers including transcription factor Oct4, alkaline phosphatase (AP), stage-specific embryonic antigen SSEA-1, stage-specific embryonic antigen SSEA-3, stage-specific embryonic antigen SSEA-4, transcription factor NANOG, tumor rejection antigen 1-60 (TRA-1-60), tumor rejection antigen 1-81 (TRA-1-81), SOX2, or REX1.

B. Induced Pluripotent Stem Cells

In other aspects, the pluripotent stem cells used herein are induced pluripotent stem (iPS) cells, commonly abbreviated iPS cells or iPSCs. The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. The use of iPSCs circumvents most of the ethical and practical problems associated with large-scale clinical use of ES cells, and patients with iPSC-derived autologous transplants may not require lifelong immunosuppressive treatments to prevent graft rejection.

With the exception of germ cells, any cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (U.S. Pat. No. 8,741,648; U.S. Publication No. 2015/0191697). There is no limitation on the degree of cell differentiation or the age of an animal from which cells are collected; even undifferentiated progenitor cells (including somatic stem cells) and finally differentiated mature cells can be used as sources of somatic cells in the methods disclosed herein. iPS cells can be grown under conditions that are known to differentiate human ES cells into specific cell types, and express human ES cell markers including: SSEA-1, SSEA-3, SSEA-4, TRA-1-60, and TRA-1-81.

Somatic cells can be reprogrammed to produce iPS cells using methods known to one of skill in the art. One of skill in the art can readily produce iPS cells, see for example, Published U.S. Patent Application No. 2009/0246875, Published U.S. Patent Application No. 2010/0210014; Published U.S. Patent Application No. 2012/0276636; U.S. Pat. Nos. 8,058,065; 8,129,187; PCT Publication NO. WO 2007/069666 A1, U.S. Pat. Nos. 8,268,620; 8,546,140; 9,175,268; 8,741,648; U.S. Patent Application No. 2011/0104125, and U.S. Pat. No. 8,691,574, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized or Oct3/4, Sox2, Nanog, and Lin28.

Mouse and human cDNA sequences of these nuclear reprogramming substances are available with reference to the NCBI accession numbers mentioned in WO 2007/069666 and U.S. Pat. No. 8,183,038, which are incorporated herein by reference. Methods for introducing one or more reprogramming substances, or nucleic acids encoding these reprogramming substances, are known in the art, and disclosed for example, in U.S. Pat. Nos. 8,268,620, 8,691,574, 8,741,648, 8,546,140, in published U.S. Pat. Nos. 8,900,871 and 8,071,369, which are both incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF. Other methods for the culture and maintenance of iPSCs, as would be known to one of skill in the art, may be used with the methods disclosed herein.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™/Essential 8™ medium (Chen et al., 2011).

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments, plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. In particular aspects, the plasmids do not comprise a tyrosinase enhancer or promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, and U.S. application Ser. No. 12/478,154 which are incorporated herein by reference.

An episomal gene delivery system can be a plasmid, an Epstein-Barr virus (EBV)-based episomal vector (U.S. Pat. No. 8,546,140), a yeast-based vector, an adenovirus-based vector, a simian virus 40 (SV40)-based episomal vector, a bovine papilloma virus (BPV)-based vector, or a lentiviral vector. A viral gene delivery system can be an RNA-based or DNA-based viral vector (PCT/JP2009/062911, PCT/JP2011/069588).

C. Embryonic Stem Cells Derived by Somatic Cell Nuclear Transfer

Pluripotent stem cells for producing the cardiac cells could also be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo.

D. MHC Haplotype Matching

Major Histocompatibility Complex is the main cause of immune-rejection of allogeneic organ transplants. There are three major class I MHC haplotypes (A, B, and C) and three major MHC class II haplotypes (DR, DP, and DQ). The HLA loci are highly polymorphic and are distributed over 4 Mb on chromosome 6. The ability to haplotype the HLA genes within the region is clinically important since this region is associated with autoimmune and infectious diseases and the compatibility of HLA haplotypes between donor and recipient can influence the clinical outcomes of transplantation. HLAs corresponding to MHC class I present peptides from inside the cell and HLAs corresponding to MHC class II present antigens from outside of the cell to T-lymphocytes. Incompatibility of MHC haplotypes between the graft and the host triggers an immune response against the graft and leads to its rejection. Thus, a patient can be treated with an immunosuppressant to prevent rejection. HLA-matched stem cell lines may overcome the risk of immune rejection.

Because of the importance of HLA in transplantation, the HLA loci are usually typed by serology and PCR for identifying favorable donor-recipient pairs. Serological detection of HLA class I and II antigens can be accomplished using a complement mediated lymphocytotoxicity test with purified T or B lymphocytes. This procedure is predominantly used for matching HLA-A and -B loci. Molecular-based tissue typing can often be more accurate than serologic testing. Low resolution molecular methods such as SSOP (sequence specific oligonucleotide probes) methods, in which PCR products are tested against a series of oligonucleotide probes, can be used to identify HLA antigens, and currently these methods are the most common methods used for Class II-HLA typing. High resolution techniques such as SSP (sequence specific primer) methods which utilize allele specific primers for PCR amplification can identify specific MHC alleles.

MHC compatibility between a donor and a recipient increases significantly if the donor cells are HLA homozygous, i.e. contain identical alleles for each antigen-presenting protein. Most individuals are heterozygous for MHC class I and II genes, but certain individuals are homozygous for these genes. These homozygous individuals can serve as super donors and grafts generated from their cells can be transplanted in all individuals that are either homozygous or heterozygous for that haplotype. Furthermore, if homozygous donor cells have a haplotype found in high frequency in a population, these cells may have application in transplantation therapies for a large number of individuals.

Accordingly, in some embodiments, iPSCs of the present methods can be produced from somatic cells of the subject to be treated, or another subject with the same or substantially the same HLA type as that of the patient. In one case, the major HLAs (e.g., the three major loci of HLA-A, HLA-B and HLA-DR) of the donor are identical to the major HLAs of the recipient. In some cases, the somatic cell donor may be a super donor; thus, iPSCs derived from a MHC homozygous super donor may be used to generate cardiac fibroblasts. Thus, the cardiac fibroblasts derived from a super donor may be transplanted in subjects that are either homozygous or heterozygous for that haplotype. For example, the cardiac fibroblasts can be homozygous at two HLA alleles such as HLA-A and HLA-B. As such, cardiac fibroblasts produced from super donors can be used in the methods disclosed herein, to produce cardiac fibroblasts that can potentially "match" a large number of potential recipients.

Accordingly, certain embodiments of the present disclosure provide a repository (e.g., a library) of HLA homozygous cardiac fibroblasts. The HLA haplotypes represented in a subject library can reflect the most common HLA haplotypes found in human populations, e.g., common Caucasian HLA haplotypes, common HLA haplotypes found in individuals of African ancestry, common Asian HLA haplotypes, common Hispanic HLA haplotypes, common Native American HLA haplotypes, etc. For example, a single abundant haplotype can be present in a significant proportion of a population, allowing a single HLA homozygous cell line to serve as a histocompatible donor for a significant percent of patients. A library includes one, two, three, four, five, six, seven, eight, nine, 10, 10-15, 15-20, 20-25, 25-30, or more than 30 different types of HLA homozygous cells. A subject library can include a first HLA homozygous cell homozygous for a first HLA haplotype; and at least a second HLA homozygous cell homozygous for a second HLA haplotype. A subject library can include a single cell type or can include two or more different cell types. A subject library can be catalogued, e.g., by a searchable computer database, in which information regarding the HLA haplotype, and optionally additional information such as cell surface markers, karyotype information, and the like, is stored and can be searched.

The HLA homozygous cardiac fibroblasts described herein can find use in a broad array of clinical applications involving transplantation of cells and/or tissues. The HLA homozygous cardiac fibroblasts are HLA compatible with a recipient, and therefore can be introduced into the recipient without the need for immunosuppressive therapy, or at least with reduced need for immunosuppressive therapy. A standard immunosuppressive drug regimen costs thousands of dollars per month, and can have undesirable side effects, including infections and cancers that are often life-threatening and expensive to treat. The present HLA homozygous cardiac fibroblasts thus overcome some of the obstacles currently limiting the use of human cells for clinical applications.

IV. Differentiation to Cardiac Fibroblasts

Embodiments of the present disclosure concern the differentiation of PSCs, particularly iPSCs, to cardiac progenitor cells including cardiac mesodermal cells and epicardial cells as well as cardiomyocytes and cardiac fibroblasts. A schematic in FIG. 1A shows an exemplary differentiation process which begins with using iPSCs that have been expanded on vitronectin-coated vessels with Essential 8 medium before initiating differentiation, such as large-scale differentiation in bioreactors.

A. Aggregate Formation

In some aspects, the pluripotent stem cells are differentiated to cardiac fibroblasts by first inducing the formation of aggregates along with initiating differentiation with a Wnt agonist, such as CHIR 99021. In certain aspects, upon aggregation, differentiation is initiated, and the cells begin to a limited extent recapitulate embryonic development. Though they cannot form trophectodermal tissue (which includes the placenta), cells of virtually every other type present in the organism can develop. The present disclosure may further promote cardiac lineage differentiation following aggregate formation.

Various matrix components may be used to culture the pluripotent cells including a collagen (e.g., collagen IV), laminin, vitronectin, Matrigel™, gelatin, polylysine, thrombospondin (e.g., TSP-1, -2, -3, -4 and/or -5), fibronectin, and/or ProNectin-F™. Combinations of these matrix components may provide additional benefit for promoting cell growth and cell viability. In certain embodiments, 1, 2, 3, 4, 5, 6, or more of the above matrix components may be used to culture cells. In some aspects, the pluripotent cells are cultured on a vitronectin-coated surface.

Pluripotent cells may be allowed to form embryoid bodies or aggregates as a part of the differentiation process. The formation of "embryoid bodies" (EBs), or clusters of growing cells, in order to induce differentiation generally involves in vitro aggregation of human pluripotent stem cells into EBs and allows for the spontaneous and random differentiation of human pluripotent stem cells into multiple tissue types that represent endoderm, ectoderm, and mesoderm origins.

In particular embodiments, the pluripotent stem cells are cultured in the presence of a ROCK inhibitor and a chemical agonist of the Wnt pathway, such as a GSK3 inhibitor (e.g., CHIR 99021), to stimulate the Wnt pathway. Agonists of the Wnt pathway may include CAS 853220-52-7 (2-Amino-4-

(3,4-(methylenedioxy)benzylamino)-6-(3-methoxyphenyl) pyrimidine), SB216763, CHIR 98014, TWS119, Tideglusib, SB415286, BIO, AZD2858, AZD1080, AR-A014418, TDZD-8, LY2090314, or IIVI-12. The medium may comprise the Wnt agonist, such as CHIR 99021, at a concentration of about 1-10 μM, such as about 1, 2, 3, 4, 5, 6, 7, 8, 9, or 10 μM. In particular aspects, the medium comprises the Wnt agonist, such as CHIR 99021, at a low concentration of about 2 μM. In particular aspects, the method comprises culturing the cells in the presence of about 2 μM (e.g., 1-3, 1-4, or 1-5 μM) of the Wnt agonist during aggregate formation, such as day 0 to day 1, and then in the presence a higher concentration of about 7 μM (e.g., 5-10 μM), such as on day 1 for mesoderm induction.

TABLE 1

Exemplary medium for aggregate formation.

| | Stock reagent/ Vendor (cat #) | Stock concentration | Final concentration | Amount per Liter | Unit |
|---|---|---|---|---|---|
| E8 basal | Thermo/A1517001 | 100% | 98% | 980 | mL |
| E8 supplement | Thermo/A1517001 | 50× | 1× | 20.00 | mL |
| H1152 | EMD Scientific/ 555550-20MGCN | 100 uM | 1 uM | 10.00 | mL |
| CHIR99021 | Stemgent/ 04-0004-10 | 10 mM | 2 uM | 200 | uL |

ROCK inhibitors may be used for culturing and passaging of pluripotent stem cells and/or differentiation of the stem cells. Therefore, ROCK inhibitors could be present in any cell culture medium in which pluripotent stem cells grow, dissociate, form aggregates, or undergo differentiation, such as an adherent culture or suspension culture. Rho-specific inhibitors, such as Clostridium botulinum C3 exoenzyme, and/or Myosin II-specific inhibitors may also be used as a ROCK inhibitor in certain aspects of the present disclosure. In specific aspects, myosin II inhibitors, such as blebbistatin, can be used to induce aggregate formation.

An exemplary ROCK-specific inhibitor is Y-27632, which selectively targets ROCK1 (but also inhibits ROCK2), as well as inhibits TNF-α and IL-1β. It is cell permeable and inhibits ROCK1/ROCK2 ($IC_{50}$=800 nM) by competing with ATP. Other ROCK inhibitors include, e.g., H1152, Y-30141, Wf-536, HA-1077, hydroxyl-HA-1077, GSK269962A and SB-772077-B. In particular aspects, the ROCK-specific inhibitor used in the present methods is H1152. In some aspects, H1152 is present in the culture at a concentration of 1-10 μM, such as about 1 μM.

Other non-limiting examples of ROCK inhibitors include antisense nucleic acids for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can be also used in embodiments (for example, refer to U.S. Patent Publication Nos. 20050209261, 20050192304, 20040014755, 20040002508, 20040002507, 20030125344 and 20030087919, and International Patent Publication Nos. 2003/062227, 2003/059913, 2003/062225, 2002/076976 and 2004/039796, which are hereby incorporated by reference). In the present methods, a combination of one or two or more of the ROCK inhibitors can also be used.

According to some embodiments, the PSCs can be treated with a ROCK inhibitor in a medium. Thereby, the medium used in the methods of the present disclosure may already contain the ROCK inhibitor or alternatively, the methods of the present disclosure may involve a step of adding the ROCK inhibitor to the medium. The concentration of the ROCK inhibitor in the medium is particularly not limited as far as it can achieve the desired effects such as the improved survival rate of stem cells. Such a ROCK inhibitor, e.g., Y-27632, HA-1077, or H-1152, may be used at an effective concentration of at least or about 0.02, 0.05, 0.1, 0.2, 0.5, 1, 2, 3, 4, 5, 10, 15, 20, 25, 30, 35, 40, 45, 50, 100, 150, 200, 500 to about 1000 μM, or any range derivable therein. These amounts may refer to an amount of a ROCK inhibitor individually or in combination with one or more ROCK inhibitors.

For example, when Y-27632 is used as the ROCK inhibitor, it can be used at the concentration of about 0.01 to about 1000 μM, more specifically about 0.1 to about 100 μM, further more specifically about 1.0 to about 30 μM, and most specifically about 2.0 to 20 μM, or any range derivable therein. When Fasudil/HA1077 is used as the ROCK inhibitor, it can be used at about twofold the aforementioned Y-27632 concentration. When H1152 is used as the ROCK inhibitor, it can be used at about 1/50th of the aforementioned Y-27632 concentration.

The aggregate formation step is performed for a duration of time sufficient to induce the production of aggregates. For example, the pluripotent stem cells, such as induced pluripotent stem cells, may be contacted with the ROCK inhibitor for about 10, 15, 20, 25, 30 minutes to several hours (e.g., at least or about one hour, two hours, three hours, four hours, five hours, six hours, eight hours, 12 hours, 16 hours, 24 hours, 36 hours, 48 hours, or any range derivable therein). In particular aspects, a period of 1-3 days, such as about 1 day, is sufficient to induce the cells to form aggregates.

The density of the stem cell(s) to be treated with the ROCK inhibitor is particularly not limited as far as it is a density at which the desired effects such as the improved survival rate of stem cells can be achieved. It is, for example, about $1.0\times10^1$ to $1.0\times10^7$ cells/ml, more particularly about $1.0\times10^2$ to $1.0\times10^7$ cells/ml, further more particularly about $1.0\times10^3$ to $1.0\times10^7$ cells/ml, and most particularly about $3.0\times10^4$ to $2.0\times10^6$ cells/ml.

In certain embodiments, PSCs are cultured in the presence of ROCK inhibitors to improve survival at low density (dissociated into single cells or small aggregates), cloning efficiency or passaging efficiency. In certain embodiments, the PSCs are cultured in the absence of feeder cells, feeder cell extracts and/or serum. The PSCs can be cultured in the presence of a ROCK inhibitor prior to subcloning or passaging, e.g., for at least one hour before subcloning or passaging. Alternatively or additionally, the PSCs are maintained in the presence of a ROCK inhibitor during or after subcloning or passaging.

Pluripotent stem cells may be seeded into aggregate promotion medium using any method known in the art of cell culture. For example, pluripotent stem cells may be seeded as a single colony or clonal group into aggregate promotion medium, and pluripotent stem cells may also be seeded as essentially individual cells. In some embodiments, pluripotent stem cells are dissociated into essentially individual cells using mechanical or enzymatic methods known in the art. By way of non-limiting example, pluripotent stem cells may be exposed to a proteolytic enzyme which disrupts the connections between cells and the culturing surface and between the cells themselves. Enzymes which may be used to individualize pluripotent stem cells for aggregate formation and differentiation may include, but are not limited to, trypsin, in its various commercial formulations, such as TrypLE, or a mixture of enzymes such as Accutase®.

In certain embodiments, pluripotent cells may be added or seeded as essentially individual (or dispersed) cells to a culturing medium for culture formation on a culture surface. The culturing medium into which cells are seeded may comprise Essential 8 (E8) medium, a survival factor, such as ROCK inhibitor, and a Wnt pathway agonist. In these embodiments, a culturing surface may be comprised of essentially any material which is compatible with standard aseptic cell culture methods in the art, for example, a non-adherent surface. A culturing surface may additionally comprise a matrix component (e.g., vitronectin) as described herein. In certain embodiments, a matrix component may be applied to a culturing surface before contacting the surface with cells and medium.

B. Mesoderm Induction

Next, the pluripotent stem cell aggregates, such as iPS cell aggregates, may be cultured in medium to promote mesoderm induction. The aggregates may be contacted with a Wnt agonist, and optionally an Activin/Nodal agonist and/or BMP. In particular aspects, the medium does not comprise a ROCK inhibitor or insulin. The medium may comprise a higher concentration of one or more Wnt agonists as compared to the aggregate formation step. The Wnt agonist may be the same as the Wnt agonist in the aggregate formation step or may be a different Wnt agonist. Agonists of the Wnt pathway may include CHIR 99021, IWP-1, IWP-2, IWP-3, IWP-4, CAS 853220-52-7 (2-Amino-4-(3,4-(methylenedioxy)benzylamino)-6-(3-methoxyphenyl)pyrimidine), SB216763, CHIR 98014, TWS119, Tideglusib, SB415286, BIO, AZD2858, AZD1080, AR-A014418, TDZD-8, LY2090314, or IM-12. The Wnt agonist may be CHIR 99021 and may be present at a concentration of about 1-10 μM, such as about 1, 2, 3, 4, 5, 6, 7, 8, 9, or 10 μM. In particular aspects, the Wnt agonist is CHIR 99021 and is present at a concentration of about 6-8 μM, such as about 6, 6.5, 7, 7.5, or 8 μM, specifically about 7 μM.

An activin agonist is a compound which activates the Activin/Nodal signaling pathway, for example by binding to TGFβ or activin receptors. Examples of activin agonists include activin A, activin B, activin AB, TGFβ1, Growth and Differentiation Factor (GDF)-3, BML-284 and Nodal. In particular aspects, the activin agonist is Activin A, such as at a concentration of about 5-20, such as 10-20 ng/mL, particularly about 12 ng/mL, specifically about 9 ng/mL. For example, BMP, such as BMP4, may be used at a concentration of 0.1 ng/mL to 10 ng/mL, particularly about 5 ng/mL.

TABLE 2

Exemplary First Mesoderm Induction Media.

| | Stock reagent/ Vendor (cat #) | Stock concentration | Final concentration | Amount per Liter | Unit |
|---|---|---|---|---|---|
| RPMI 1640 | Thermo/ 11875093 | 100% | 98% | 980 | mL |
| B27 (-Insulin) | Thermo/ A1895601 | 50× | 1× | 20 | mL |
| CHIR99021 | Stemgent/ 04-0004-10 | 10 mM | 6-8 uM | 700 | uL |

TABLE 2-continued

Exemplary First Mesoderm Induction Media.

| | Stock reagent/ Vendor (cat #) | Stock concentration | Final concentration | Amount per Liter | Unit |
|---|---|---|---|---|---|
| Activin A | R&D Systems/ 338-AC | 25 ug/mL | 9 ng/ml | 360 | uL |
| BMP4 | R&D Systems/ 314-BP (Solution | 25 ug/mL | 5 ng/ml | 200 | uL |

In some aspects, the mesoderm induction comprises a first step comprises a Wnt agonist, activin agonist, and BMP (e.g., for about 1 day) followed by a second step comprises an activin agonist and BMP without the presence of a Wnt agonist (e.g., for about 1-3 days, particularly about 2 days).

TABLE 3

Exemplary Second Mesoderm Induction Media.

| | Stock reagent/ Vendor (cat #) | Stock concentration | Final concentration | Amount per Liter | Unit |
|---|---|---|---|---|---|
| RPMI-1640 | Thermo/11875093 | 100% | 98% | 980 | mL |
| B27 (-Insulin) | Gibco/A1895601 | 50× | 1× | 20 | mL |
| Activin A | R&D Systems/ 338-AC | 25 ug/mL | 9 ng/ml | 360 | uL |
| BMP4 | R&D Systems/ 314-BP (Solution | 25 ug/mL | 5 ng/ml | 200 | uL |

The basal medium for mesoderm induction may be any medium known in the art for culturing stem cells. Exemplary medium include E8, TeSR, BME, BGJb, CMRL 1066, Glasgow MEM, Improved MEM Zinc Option, IMDM, Medium 199, Eagle MEM, αMEM, DMEM, Ham, RPMI 1640, and Fischer's media. In particular aspects, the basal medium is RPMI supplemented with B27 without insulin. In specific aspects, the media does not comprise or has essentially no insulin. In some aspects, the mesoderm induction media comprises albumin.

The mesoderm induction step may be for a period of time sufficient to induce mesoderm markers, such as CXCR4, KDR, PDGFRα, and/or CD56, as well as loss of expression of CKIT and/or EPCAM. For example, the aggregates may be cultured in the presence of Wnt agonist, Activin/Nodal agonist, and/or BMP for about 1-5 days, such as about 1, 2, 3, 4, or 5 days. In particular aspects, the aggregates are cultured for about 2-3 days for mesoderm induction.

In particular aspects, mesoderm induction in the presence of a Wnt agonist, activin agonist, and BMP produces a population comprising NCAM+CXCR4low cells and NCAM+CXCR4+ cells. In some aspects, the activin agonist and BMP results in a decrease in the percentage of CXCR4+ progenitors as compared to culturing without the activin agonist and BMP (i.e., only a Wnt agonist).

C. Cardiac Progenitor Cells

The mesoderm progenitor cells may then be directed to WT1+ progenitors (e.g., epicardial, endothelial, etc.) in the presence of a Wnt inhibitor, such as for about 1-3 days, particularly about 2 days. In particular aspects, the cardiac (e.g., epicardial, endothelial, etc.) progenitor induction is in the absence of BMP4, Wnt agonist (e.g., CHIR99021), GSK3 inhibition, and/or retinoic acid.

In some aspects, the aggregates that are at the mesoderm stage can be kept in a suspension culture system or the mesoderm cells may be individualized and plated as a monolayer culture prior to initiation of epicardial progenitor specification. In particular aspects, the aggregates are dissociated prior to culturing in the presence of a Wnt inhibitor. Aggregate dissociation can be performed using any known procedures. These procedures include treatments with a chelating agent (such as EDTA), an enzyme (such as trypsin, collagenase), or the like, and operations such as mechanical dissociation (such as pipetting). The cells may be cultured on a matrix as described above, such as a vitronectin-coated surface. In certain aspects, the differentiation process may be serum free with no drug resistant or metabolic selection used. Epicardial cells may be plated on vitronectin-coated plates.

The Wnt inhibitor may be XAV939, ICG-001, IWR-1-endo, Wnt-059, LGK-974, LF3, CP21R7, NCB-0846, PNU-74654, IWR-1, IWR-2, IWR-3, IWR-4 or KYA179K. The Wnt inhibitor, such as XAV939, may be present at a concentration of about 1-10 μM, such as about 1, 2, or 5 mM, particularly about 2 μM.

TABLE 4

Exemplary Cardiac Progenitor Induction Media.

| | Stock reagent/ Vendor (cat #) | Stock concentration | Final concentration | Amount per Liter | Unit |
|---|---|---|---|---|---|
| RPMI 1640 | Thermo/ 11875093 | 100% | 98% | 980 | mL |
| B27 (Insulin) | Gibco/A1895601 | 50× | 1× | 20 | mL |
| XAV939 X010 (MP-00230) | Sigma/X3004-5 mg or Sigma/X3004-25 mg | 16 mM | 2 uM | 125 | uL |

To support the WT1+ cardiac (e.g., epicardial) progenitor cells, the cells may be cultured in the presence of a TGFβ inhibitor, such as for about 5-20 days, to produce a mixture of epicardial progenitors and cardiomyocytes. The media may further comprise ascorbic acid. In particular aspects, the epicardial progenitor culture is in the absence of BMP4, Wnt agonist (e.g., CHIR99021), GSK3 inhibition, and/or retinoic acid. In specific aspects, the epicardial cells are cultured without Wnt modulation. In particular aspects, the epicardial cells may be directly used for cardiac fibroblast induction without any additional purification steps.

The TGFβ inhibitor may be SB431542, LDN-193189, LY2157299, LY2109761, SB525334, SIS HCl, SB505124, GW788388, or LY364947. The TGFβ inhibitor, such as SB431542, may be present at a concentration of about 1-25 mM, such as about 5, 10, or 15 mM, particularly about 10 mM. 193189, LY2157299, LY2109761, SB525334, SIS HCl, SB505124, GW788388, or LY364947. The TGFβ inhibitor, such as SB431542, may be present at a concentration of about 1-10 μM, such as about 4, 5, or 6 μM, particularly about 5 μM.

TABLE 5

Exemplary Cardiac (e.g., Epicardial) Media.

| | Stock reagent/ Vendor (cat #) | Stock concentration | Final concentration | Amount per Liter | Unit |
|---|---|---|---|---|---|
| DMEM/F12 | Thermo/ 1133032 | 100% | 90% | 1000 | mL |
| SB43152 | Sigma S4317 or Tocris/1614 (MP-S040) MP-00206 (S050) | 40 mM | 5 μM | 125 | μl |

TABLE 5-continued

Exemplary Cardiac (e.g., Epicardial) Media.

| | Stock reagent/ Vendor (cat #) | Stock concentration | Final concentration | Amount per Liter | Unit |
|---|---|---|---|---|---|
| Ascorbic Acid | Sigma/49752 | 50 mg/mL | 100 ug/ml | 2 | mL |
| Gentamicin | Gibco/5750 | 50 mg/mL | 25 μg/mL | 500 | μL |

D. Cardiac Fibroblast Induction

The WT1+ cardiac (e.g., epicardial) progenitor cells may then be cultured in the absence of a TGFβ inhibitor for cardiac fibroblast induction. The cardiac fibroblast induction may comprise basic FGF (bFGF), such as at a concentration of 10-500 ng/mL, such as about 10, 25, 40, 50, 75, 100, 150, 200, 250, 300, 400, or 500 ng/mL. In particular aspects, the cardiac fibroblast induction is performed essentially in the absence of a TGFβ inhibitor.

In some aspects, the cardiac fibroblast induction is in the presence of serum, such as fetal bovine serum (e.g., about 5-15%, particularly about 10%). The bFGF may be present at about 150-200 ng/mL. The cells may be passaged about 3-5 times to purify the cardiac fibroblasts to obtain quiescent cardiac fibroblasts with more than 75% expression for TE-7 and less than 5% expression of αSMA.

Integrin beta-1 (ITGB1), also known as CD29, is a cell surface receptor that in humans is encoded by the ITGB1 gene. Cardiac fibroblasts differentiated by this method can have increasing expression of CD29, such as at least 75% or 85% expression of CD29. In cardiac muscle and skeletal muscle, the integrin beta-1D isoform of CD29 is specifically expressed.

TABLE 6

Exemplary Serum Cardiac Fibroblast Induction Media.

| Cardiac Fibroblast Induction Medium | Stock reagent/ Vendor (cat #) | Stock concentration | Final concentration | Amount per Liter | Unit |
|---|---|---|---|---|---|
| DMEM Low Glucose | HyClone (GE)/ SH30021 or Fisher (Gibco)/10567 | 100% | 90% | 900 | mL |
| Fetal Bovine Serum | HyClone (GE)/ SH30071 or Fisher (Gibco)/ | 100% | 10% | 100 | mL |
| bFGF | Peprotech/ 1105532 or Zebrafish-bFGF Promega/ 9260010495 | 1 mg/mL | 200 ng/ml | 200 | μL |
| Ascorbic Acid | Sigma/49752 | 50 mg/mL | 100 ug/ml | 2 | mL |
| Gentamicin | Gibco/15750 | 50 mg/mL | 25 μg/mL | 500 | μL |

In other aspects, the cardiac fibroblast induction is in the absence of serum. The bFGF may be present at about 5-200 ng/mL, particularly about 40 ng/mL. The culture may further comprise BSA, vascular endothelial growth factor (VEGF), insulin-like growth factor (IGF), epidermal growth factor (EGF), hydrocortisone, and heparin. The cells may be passaged about 3-5 times to purify the cardiac fibroblasts to obtain quiescent cardiac fibroblasts with more than 75% expression for TE-7 and less than 5% expression of αSMA.

TABLE 7

Exemplary Serum-free Cardiac Fibroblast Induction Media.

| Co-culture Medium | Stock reagent/ Vendor (cat #) | Stock concen-tration | Final concen-tration | Amount per Liter | Unit |
|---|---|---|---|---|---|
| DMEM no glucose | Gibco/11956 | 100% | 80% | 800 | mL |
| Dialyzed FBS | Hyclone/SH30079.03 | 100% | 8% | 8 | mL |
| Galactose | Sigma /G5388 | solid | 8 mM | 144 | g |
| Sodium Pyruvate | Sigma/P4562 | solid | 0.8 mM | 0.088 | g |
| IMDM (+glutamine) | Gibco/12440053 | 100% | 20% | 200 | mL |
| BSA (30% solution) | Sigma/A9576 | 30% | 0.40% | 1.32 | mL |
| VEGF-165 | Sigma/H9166 | 0.025 mg/mL | 8 ng/ml | 320 | uL |
| zbFGF | Promega/9260010495 | 1 mg/mL | 2 ng/ml | 2 | uL |
| EGF | Life Technologies/ PHG0311 | 1 mg/mL | 5 ng/ml | 10 | uL |
| IGF | Sigma/91590C | 1 mg/mL | 40 ng/mL | 40 | uL |

The cardiac fibroblast cells may be cryopreserved, such as between passage 5 and 15. The cryopreserved cardiac fibroblast cells may be used for cardiac tri-culture microtissue and other assays. The cardiac fibroblasts may be cultured in the presence of cardiomyocytes and endothelial cells. The co-culture media may comprise BSA, VEGF, bFGF, EGF, and/or IGF. In some aspects, the media does not comprise VEGF.

TABLE 8

Exemplary Co-culture Media.

| Co-culture Medium | Stock reagent/ Vendor (cat #) | Stock concen-tration | Final concen-tration | Amount per Liter | Unit |
|---|---|---|---|---|---|
| DMEM no glucose | Gibco/11956 | 100% | 80% | 800 | mL |
| Dialyzed FBS | Hyclone/SH30079.03 | 100% | 8% | 8 | mL |
| Galactose | Sigma/G5388 | solid | 8 mM | 144 | g |
| Sodium Pyruvate | Sigma/P4562 | solid | 0.8 mM | 0.088 | g |
| IMDM (+glutamine) | Gibco/12440053 | 100% | 20% | 200 | mL |
| BSA (30% solution) | Sigma/A9576 | 30% | 0.40% | 13.33 | uL |
| VEGF-165 | Sigma/H9166 | 1 mg/mL | 8 ng/ml | 1.6 | uL |
| zbFGF | Promega/9260010495 | 1 mg/mL | 2 ng/ml | 0.4 | uL |
| EGF | LifeTechnologies/ PHG0311 | 1 mg/mL | 5 ng/ml | 1 | uL |
| IGF | Sigma/91590C | 1 mg/mL | 40 ng/ml | 8 | uL |

The cardiac fibroblasts may be activated in the presence of TGFβ, such as on vitronectin-coated plates. The cardiac fibroblasts may be characterized by measuring fibronectin secretion.

E. Cell Culture Conditions

The culturing conditions according to the present disclosure will be appropriately defined depending on the medium and stem cells used. The medium according to the present disclosure can be prepared using a medium to be used for culturing animal cells as its basal medium. As the basal medium, any of E8, TeSR, BME, BGJb, CMRL 1066, Glasgow MEM, Improved MEM Zinc Option, IMDM, Medium 199, Eagle MEM, αMEM, DMEM, Ham, RPMI 1640, and Fischer's media, as well as any combinations thereof can be used, but the medium is not particularly limited thereto as far as it can be used for culturing animal cells.

In particular aspects, the medium according to the present disclosure is a serum-free medium. The serum-free medium refers to media with no unprocessed or unpurified serum and accordingly, can include media with purified blood-derived components or animal tissue-derived components (such as growth factors). The medium according to the present disclosure may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolgiycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium of the present disclosure can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the stem cell(s).

A culture vessel used for culturing the stem cell(s) can include, but is particularly not limited to: flask, flask for tissue culture, dish, petri dish, dish for tissue culture, multi dish, micro plate, micro-well plate, multi plate, multi-well plate, micro slide, chamber slide, tube, tray, CellSTACK® Chambers, culture bag, roller bottle, and bioreactors, such as PBS500 and/or PBS3, as long as it is capable of culturing the stem cells therein. The stem cells may be culture in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, 2000 ml, or any range derivable therein, depending on the needs of the culture. In a certain embodiment, the culture vessel may be a bioreactor, which may refer to any device or system that supports a biologically active environment. The bioreactors may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, laminin, and fibronectin and mixtures thereof for example Matrigel™, and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The CO 2 concentration can be about 1 to 10%, for example, about 2 to 5%, or any range derivable therein. The oxygen tension can be at least or about 1, 5, 8, 10, 20%, or any range derivable therein.

The methods of the present disclosure can be also used for a suspension culture of stem cells, including suspension culture on carriers (Fernandes et al., 2007) or gel/biopolymer encapsulation (United States Patent 20070116680). The term suspension culture of the stem cells means that the stem cells are cultured under non-adherent condition with respect to the culture vessel or feeder cells (if used) in a medium. The suspension culture of stem cells includes a dissociation culture of stem cells and an aggregate suspension culture of stem cells. The term dissociation culture of stem cells means that suspended stem cells is cultured, and the dissociation culture of stem cells include those of single stem cell or those of small cell aggregates composed of a plurality of stem cells (for example, about 2 to 400 cells). When the aforementioned dissociation culture is continued, the cultured, dissociated cells form a larger aggregate of stem cells, and thereafter an aggregate suspension culture can be performed. The aggregate suspension culture includes an embryoid culture method (see Keller et al., 1995), and a SFEB method (Watanabe et al., 2005); International Publication No. 2005/123902). The methods of the present disclosure can significantly improve the survival rate and/or differentiation efficiency of stem cells in a suspension culture.

Bioreactors can be grouped according to general categories including: static bioreactors, stirred flask bioreactors, rotating wall vessel bioreactors, hollow fiber bioreactors and direct perfusion bioreactors. Within the bioreactors, cells can be free, or immobilized, seeded on porous 3-dimensional scaffolds (hydrogel). In certain aspects, the bioreactor is a suspension bioreactor for efficient mixing with homogeneous particle suspension and low shear stress.

The methods disclosed utilized herein may use all GMP compatible materials and be scaled to multiple (e.g., 3 L) bioreactor manufacturing batches to yield the purity and cell numbers needed for cardiac cell therapy development.

F. Characterization of Cardiac Fibroblast Cells

The cells obtained according to the present methods can be characterized according to a number of phenotypic criteria. The quiescent cardiac fibroblasts may be characterized by expression for fibroblast marker TE-7, CD29, and/or CD90. They are notably negative for alpha-smooth muscle actin by qPCR and flow cytometry. In some cases there may be less than <5% of cells positive for alpha smooth muscle actin. They may have a spindle morphology with multiple processes emanating from the cell body and a pronounced, round nucleus.

Cardiomyocytes and precursor cells derived from pluripotent stem cell lines often have morphological characteristics of cardiomyocytes from other sources. They can be spindle, round, triangular or multi-angular shaped, and they may show striations characteristic of sarcomeric structures detectable by immunostaining. They may form flattened sheets of cells, or aggregates that stay attached to the substrate or float in suspension, showing typical sarcomeres and atrial granules when examined by electron microscopy.

Pluripotent stem cell-derived cardiac fibroblasts and their precursors typically have at least one of the cardiomyocyte specific markers including cardiac troponin I (cTnI), a subunit of troponin complex that provides a calcium-sensitive molecular switch for the regulation of striated muscle contraction, cardiac troponin T (cTnT), or Nkx2.5, a cardiac transcription factor expressed in cardiac mesoderm during early mouse embryonic development, which persists in the developing heart. The cells will also typically express at least one (and often at least 3, 5, or more) of the markers including Atrial natriuretic factor (ANF), myosin heavy chain (MHC), particularly the 13 chain which is cardiac specific, MLC, Titin, tropomyosin, α-sarcomeric actinin, and desmin ANF is a hormone expressed in developing heart and fetal cardiomyocytes but down-regulated in adults. It is considered a good marker for cardiomyocytes because it is expressed in a highly specific manner in cardiac cells but not skeletal myocytes. Additional markers include MEF-2A, MEF-2B, MEF-2C, MEF-2D (transcription factors that are expressed in cardiac mesoderm and persist in developing heart), N-cadherin, which mediates adhesion among cardiac cells, Connexin 43, which forms the gap junction between cardiomyocytes, β1-adrenoceptor (β1-AR), creatine kinase MB (CK-MB) and myoglobin, which are elevated in serum following myocardial infarction, α-cardiac actin, early growth response-I, cyclin D2, and GATA-4, a transcription factor that is highly expressed in cardiac mesoderm and persists in the developing heart. It regulates many cardiac genes and plays a role in cardiogenesis.

In the present studies, pluripotent stem cell-derived cardiac fibroblasts expressed characteristic markers of fibroblasts such as vimentin (VIM), extracellular matrix proteins such as collagens (COL1A1 and COL1A2) and genes that modulate procollagen processing collagen such as secreted protein acidic and rich in cysteine (SPARC). Secretion of collagen 1A and fibronectin were measured by ELISA under quiescent and TGFβ activated conditions. Due to cardiac fibroblasts role in maintaining the extracellular matrix of the heart, pluripotent stem cell-derived cardiac fibroblasts express matrix metalloproteinases such as MMPs (MMP1, MMP2, MMP14) and tissue inhibitors of matrix metalloproteases including (TIMP1 and TIMP3) were highly expressed. iPSC cardiac fibroblasts generated by the present methods were >85% positive for THY-1 (CD90) by flow cytometry. Additional markers include MEF-2A, MEF-2C, MEF-2D (transcription factors that are expressed in cardiac mesoderm and persist in developing heart), N-cadherin (CDH2), which mediates adhesion among cardiac cells, and importantly connexin 43 (GJA1), which forms the gap junction between cardiomyocytes and cardiac fibroblasts throughout the heart.

In further studies of the present methods, single cell RNA sequencing studies showed a heterogeneity of the cardiac fibroblast population. During embryonic development cardiac fibroblasts can arise from up to four different sources: epicardial, endocardial/endothelial, neural crest, and second heart field progenitors. Cardiac fibroblasts carry the transcription factor code of their developmental lineage. The single cell data of the cardiac fibroblast cells produced by the present AB methods showed are a heterogeneous population. The studies showed expression of discoidin domain receptor 2 (DDR2) and periostin (POSTN) by bulk RNA sequencing and in subsets of our iPSC derived cardiac fibroblasts. About 50% of the present cardiac fibroblasts expressed GATA-4, a transcription factor that is highly expressed in cardiac mesoderm and persists in the developing heart. It regulates many cardiac genes and plays a role in cardiogenesis. It was also shown that about 50% of the cardiac fibroblasts expressed second heart field marker HAND2. It was also observed that 33% of the cardiac fibroblasts expressed the endocardial/endothelial fibroblasts progenitor's marker Tie2 (TEK). Between 10-20% of the cardiac fibroblasts expressed WT1, SNAIL TBX18, and TBX20 indicating that they were from an epicardial lineage. Expression of the cardiac transcription factor WT1 was observed in early passages, however, WT1 decreased with passaging. Less than 3% of the cardiac fibroblasts produced by this method were positive for neural crest marker Pax3. Additionally, cardiac transcription factors Nkx2-5 and Isl1 were expressed in less than 2% of cells. Furthermore, few cardiac fibroblasts <2% expressed the characteristic quiescent cardiac fibroblast marker TCF21.

Interestingly, a population of 66% cardiac fibroblasts was observed to express sinoatrial node associated markers including T-box transcription factor 3 (TBX3) and a subpopulation of those also expressed connexin 45 (GCA1). Connexin 45 connects cardiomyocytes and cardiac fibroblasts in the sinoatrial node.

In some aspects, the cardiac fibroblasts are cell-surface markers, PDGFRa-positive and PDGFRb-positive cardiac fibroblast cells indicating a potential for these cell to have a more pericyte morphology made up two subpopulations of cardiac fibroblasts.

Gene expression analysis and flow cytometery of cardiac fibroblasts for alpha smooth muscle actin showed a very small <5% positive population. Total RNA sequencing showed that levels of ACTA2 were comparable in adult primary cardiac fibroblasts, fetal primary cardiac fibroblasts, and iPSC derived cardiac fibroblasts. The level of TCF21 was lower in iPSC derived cardiac fibroblsts than the primary counterparts. Levels of extracellular matrix proteins were similar across all of the fibroblasts types. Single cell RNA-sequencing revealed a population of 38% of alpha smooth muscle actin cells with an expression level greater than zero. There were two populations of ACTA2 cells as has been shown in the literature. The high expressing population clustered with activation markers and constituted 5-10% of the cells.

Tissue-specific markers can be detected using any suitable immunological technique—such as flow immunocytometry or affinity adsorption for cell-surface markers, immunocytochemistry (for example, of fixed cells or tissue sections) for intracellular or cell-surface markers, Western blot analysis of cellular extracts, and enzyme-linked immunoassay, for cellular extracts or products secreted into the medium. Antibodies that distinguish cardiac markers like GATA4 and HAND2 or fibroblasts markers such as Vimentin, CD90, or DDR2 from other isoforms are available commercially from suppliers like Sigma and Spectral Diagnostics. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody.

The expression of tissue-specific gene products can also be detected at the mRNA level by Northern blot analysis, dot-blot hybridization analysis, RNA sequencing (e.g., single cell), or by reverse transcriptase initiated polymerase chain reaction (RT-PCR) using sequence-specific primers in standard amplification methods using publicly available sequence data (GenBank). Expression of tissue-specific markers as detected at the protein or mRNA level is considered positive if the level is at least or about 2-, 3-, 4-, 5-, 6-, 7-, 8-, or 9-fold, and more particularly more than 10-, 20-, 30, 40-, or 50-fold above that of a control cell, such as an undifferentiated pluripotent stem cell or other unrelated cell type.

Tissue-specific markers can be detected using any suitable immunological technique—such as flow immunocytometry or affinity adsorption for cell-surface markers, immunocytochemistry (for example, of fixed cells or tissue sections) for intracellular or cell-surface markers, Western blot analysis of cellular extracts, and enzyme-linked immunoassay, for cellular extracts or products secreted into the medium. Antibodies that distinguish cardiac markers like cTnI and cTnT from other isoforms are available commercially from suppliers like Sigma and Spectral Diagnostics. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods using publicly available sequence data (GenBank). Expression of tissue-specific markers as detected at the protein or mRNA level is considered positive if the level is at least or about 2-, 3-, 4-, 5-, 6-, 7-, 8-, or 9-fold, and more particularly more than 10-, 20-, 30, 40-, or 50-fold above that of a control cell, such as an undifferentiated pluripotent stem cell or other unrelated cell type.

Once markers have been identified on the surface of cells of the desired phenotype, they can be used for immunoselection to further enrich the population by techniques such as immunopanning or antibody-mediated fluorescence-activated cell sorting.

Functional attributes provide a manner of characterizing cells and their precursors in vitro, but may not be necessary for some of the uses referred to in this disclosure. For example, a mixed cell population enriched for cells bearing some of the markers listed above, but not all of the functional or electrophysiology properties, can be of considerable therapeutic benefit if they are capable of grafting to impaired cardiac tissue, and acquiring in vivo the functional properties needed to supplement cardiac function.

Where derived from an established line of pluripotent stem cells, the cell populations and isolated cells of the present disclosure can be characterized as having the same genome as the line from which they are derived. This means that the chromosomal DNA will be over 90% identical between the pluripotent stem cells and the cardiac cells, which can be inferred if the cardiac cells are obtained from the undifferentiated line through the course of normal mitotic division. The characteristic that cardiac lineage cells are derived from the parent cell population is important in several respects. In particular, the undifferentiated cell population can be used for producing additional cells with a shared genome—either a further batch of cardiac cells, or another cell type that may be useful in therapy—such as a population that can pre-tolerize the patient to the histocompatibility type of the cardiac allograft (US 2002/0086005; WO 03/050251).

V. Methods of Use

The cardiac fibroblast cells provided by methods and compositions of certain aspects can be used in a variety of applications. These include but are not limited to transplantation or implantation of the cells in vivo; screening cytotoxic compounds, carcinogens, mutagens growth/regulatory factors, pharmaceutical compounds, etc., in vitro; elucidating the mechanism of cardiac diseases and injuries; studying the mechanism by which drugs and/or growth factors operate; diagnosing and monitoring cancer in a patient; gene therapy; and the production of biologically active products.

Cardiac fibroblast cells of the present disclosure can be used commercially to screen for factors (such as solvents, small molecule drugs, peptides, oligonucleotides) or environmental conditions (such as culture conditions or manipulation) that affect the characteristics of such cells and their various progeny.

The cardiac fibroblasts may be used in a tri-culture assay with endothelial cells and fibroblasts for in vitro disease modelling, drug discovery, and toxicity testing.

In some aspects, cardiac fibroblast cells are used to screen factors that promote maturation into later-stage cardiac cells, or terminally differentiated cells, or to promote proliferation and maintenance of such cells in long-term culture. For example, candidate maturation factors or growth factors are tested by adding them to cells in different wells, and then determining any phenotypic change that results, according to desirable criteria for further culture and use of the cells.

Other screening applications of the present disclosure relate to the testing of pharmaceutical compounds for their effect on cardiac fibrosis and/or heart failure. Screening may be done either because the compound is designed to have a pharmacological effect on the cells, or because a compound designed to have effects elsewhere may have unintended side effects on cells of this tissue type. The screening can be conducted using any of the precursor cells or terminally differentiated cells of the disclosure.

The reader is referred generally to the standard textbook. In vitro Methods in Pharmaceutical Research, Academic Press, 1997, and U.S. Pat. No. 5,030,015. Assessment of the activity of candidate pharmaceutical compounds generally involves combining the differentiated cells of this disclosure with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to Vickers (pp 375-410 in In vitro Methods in Pharmaceutical Research, Academic Press, 1997) for further elaboration.

Effect of cell function can be assessed using any standard assay to observe phenotype or activity of cardiomyocytes, such as marker expression, receptor binding, contractile activity, or electrophysiology—either in cell culture or in vivo. Pharmaceutical candidates can also be tested for their effect on contractile activity—such as whether they increase or decrease the extent or frequency of contraction. Where an effect is observed, the concentration of the compound can be titrated to determine the median effective dose ($ED_{50}$).

The present disclosure further provides methods for screening for agents that have an effect on cardiomyocytes, endothelial cells, and cardiac fibroblasts. The method comprises contacting cells from one of the cell populations described hereinabove with a candidate agent, and determining whether the agent has an effect on the cell population. The agent to be tested may be natural or synthetic, one compound or a mixture, a small molecule or polymer including polypeptides, polysaccharides, polynucleotides and the like, an antibody or fragment thereof, a compound from a library of natural or synthetic compounds, a compound obtained from rational drug design, a condition such as a cell culture condition, or any agent the effect of which on the cell population may be assessed using assays known in the art. The effect on the cell population may be determined by any standard assay for phenotype or activity, including for example an assay for marker expression, receptor binding, contractile activity, electrophysiology, cell viability, survival, morphology, or DNA synthesis or repair. Standard proliferation and differentiation assays are described in U.S. Pat. No. 6,110,739. Such agents are useful for the control of cell growth, differentiation and survival in vivo and in vitro, and tissue maintenance, regeneration and repair.

A. Pharmaceutical Compositions

The present disclosure further provides compositions comprising populations of cardiac fibroblast cells. The compositions may further comprise populations of cardiomyocytes. The compositions may comprise pharmaceutically acceptable carriers and diluents. The compositions may further comprise components that facilitate engraftment. Compositions comprising these populations are useful for cell and tissue replacement and repair, and for generating populations of cardiac fibroblasts in vitro and in vivo. The compositions may be formulated as a medicament or delivery device for treating a cardiac condition.

The cardiac fibroblast cells of the present disclosure can be supplied in the form of a pharmaceutical composition, comprising an isotonic excipient prepared under sufficiently sterile conditions for human administration. In certain aspects, it may be desirable to disperse the cells using a protease or by gentle mechanical manipulation into a suspension of single cells or smaller clusters. To reduce the risk of cell death upon engraftment, the cells may be treated by heat shock or cultured with about 0.5 U/mL erythropoietin about 24 hours before administration.

For general principles in medicinal formulation, the reader is referred to Cell Therapy: Stem Cell Transplantation, Gene Therapy, and Cellular Immunotherapy, 1996; and Hematopoetic Stem Cell Therapy, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cardiomyocytes. Suitable ingredients include cardiac fibroblast derived matrix proteins that support or promote adhesion of the cardiomyocytes, or complementary cell types, especially endothelial cells.

This disclosure also includes a reagent system, comprising a set or combination of cells that exist at any time during manufacture, distribution, or use. The cell sets comprise any combination of two or more cell populations described in this disclosure, exemplified but not limited to a type of differentiated cell (cardiac progenitors, epicardial cells, and cardiac fibroblasts), in combination with undifferentiated pluripotent stem cells or other differentiated cell types (e.g., cardiomyocytes and endothelial cells), often sharing the same genome. Each cell type in the set may be packaged together, or in separate containers in the same facility, or at different locations, at the same or different times, under control of the same entity or different entities sharing a business relationship.

Pharmaceutical compositions of this disclosure may optionally be packaged in a suitable container with written instructions for a desired purpose, such as the reconstitution of a mixture of cardiomyocytes, cardiac fibroblasts, and endothelial cells to improve a disease condition or abnormality of the cardiac muscle.

B. Therapeutic Uses

The cells provided in certain aspects of this present disclosure can be used for therapy of any subject in need thereof. Human conditions that may be appropriate for such therapy include cardiac disorders, such as myocardial infarction, cardiomyopathy, congestive heart failure, ventricular septal defect, atrial septal defect, congenital heart defect, ventricular aneurysm, a cardiac disorder which is pediatric in origin, ventricular aneurysm, or a cardiac disorder which requires ventricular reconstruction.

For human therapy, the dose is generally between about $10^8$ and $10^{12}$ cells, and typically between about $2\times10^8$ and $1\times10^9$ cells, making adjustments for the body weight of the subject, nature and severity of the affliction, and the replicative capacity of the administered cells. The ultimate responsibility for determining the mode of treatment and the appropriate dose lies with the managing clinician.

Certain aspects also provide for the use of cardiac fibroblast cells to enhance tissue maintenance or repair of cardiac muscle for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and maintain their phenotype in vivo. Cell compositions are administered to immunodeficient animals (such as NUDE rats, or animals rendered immunodeficient chemically or by irradiation). Tissues are harvested after a period of engraftment, and assessed as to whether pluripotent stem cell-derived cells are still present.

Other methods to track cells in vivo may be by administering cells that express a detectable label (such as green fluorescent protein, or (3-galactosidase); that have been prelabeled (for example, with BrdU or [$^3$H]thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

Suitability can also be determined by assessing the degree of cardiac recuperation that ensues from treatment with a cell population of cardiac fibroblasts derived from pluripotent stem cells. A number of animal models are available for such testing. For example, hearts can be cryoinjured by placing a precooled aluminum rod in contact with the surface of the anterior left ventricle wall (Murry et al., 1996; Reinecke et al., 1999; U.S. Pat. No. 6,099,832; Reinecke et al., 2004). In larger animals, cryoinjury can be effected by placing a 30-50 mm copper disk probe cooled in liquid $N_2$ on the anterior wall of the left ventricle for about 20 min (Chiu et al., 1995). Infarction can be induced by ligating the left main coronary artery (Li et al., 1997). Injured sites are treated with cell preparations of this disclosure, and the heart tissue is examined by histology for the presence of the cells in the damaged area. Cardiac function can be monitored by determining such parameters as left ventricular end-diastolic pressure, developed pressure, rate of pressure rise, and rate of pressure decay.

After adequate testing, differentiated cells of this disclosure can be used for tissue reconstitution or regeneration in a human patient or other subject in need of such treatment. The cells are administered in a manner that permits them to graft or migrate to the intended tissue site and reconstitute or regenerate the functionally deficient area. Special devices are available that are adapted for administering cells capable of reconstituting cardiac function directly to the chambers of the heart, the pericardium, or the interior of the cardiac muscle at the desired location.

Where desirable, the patient receiving an allograft of pluripotent stem cell-derived cardiac fibroblast cells can be treated to reduce immune rejection of the transplanted cells. Methods contemplated include the administration of traditional immunosuppressive drugs like cyclosporin A (Dunn et al., Drugs 61:1957, 2001), or inducing immunotolerance using a matched population of pluripotent stem cell-derived cells (WO 02/44343; U.S. Pat. No. 6,280,718; WO 03/050251). Another approach is to adapt the cardiac fibroblast cell population to decrease the amount of uric acid produced by the cells upon transplantation into a subject, for example, by treating them with allopurinol. Alternatively or in conjunction, the patient is prepared by administering allopurinol, or an enzyme that metabolizes uric acid, such as urate oxidase (PCT/US04/42917).

Patients suitable for receiving regenerative medicine according to the present methods include those having acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, patient mobility, and quality of life.

In another embodiment, the present disclosure provides methods of cell replacement and methods of tissue replacement useful for treatment of disorders characterized by insufficient cardiac function including, for example, congenital heart disease, coronary heart disease, cardiomyopathy, endocarditis and congestive heart failure. The cardiac fibroblasts cells and the cardiovascular progenitor cells are useful for replacement therapy. Methods for engineering cardiac tissue are known in the art and reviewed for example by Birla in "Stem Cell Therapy and Tissue Engineering for Cardiovascular Repair" Springer, 2006. In a preferred embodiment, the subject is a human. The composition may be administered by a route that results in delivery to or migration to cardiac tissue including, for example, injection or implantation, and under conditions that result in a reduction of at least one adverse effect or symptom or the disorder.

With respect to the therapeutic methods of the present disclosure, it is not intended that the administration of cardiac fibroblast cells to a mammal be limited to a particular mode of administration, dosage, or frequency of dosing; the present disclosure contemplates all modes of administration, including intramuscular, intravenous, intrarticular, intralesional, subcutaneous, or any other route sufficient to provide a dose adequate to prevent or treat a disease. The cardiac fibroblast cells may be administered to the mammal in a single dose or multiple doses. When multiple doses are administered, the doses may be separated from one another by, for example, one week, one month, one year, or ten years. One or more growth factors, hormones, interleukins, cytokines, small molecules or other cells may also be administered before, during, or after administration of the cells to further bias them towards a particular cell type.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Development of Cardiac Fibroblasts

The present studies developed a differentiation method to produce highly pure populations of iPSC-derived quiescent cardiac fibroblasts, such as from a population of (WT1+) epicardial cells by addition of serum-containing medium or non-serum containing medium in the presence of basic FGF (FIG. 1).

A starting population of iPSCs were formed into aggregates in a low concentration of GSK3 inhibitor in E8 medium comprising ROCK inhibitor (Table 1). On Day 1, iPSCs were treated with a high level GSK3 (CHIR99021) inhibitor for one day in the presence of Activin A and BMP4 growth factors in RPMI/B27 minus insulin containing medium for cardiac mesoderm induction. On day two no GSK3 inhibitor was used and Activin A and BMP4 growth factors were refreshed. This is termed ABC mesoderm induction.

By Day 3, a different mesoderm progenitor population (NCAM+/CXCR4+) was generated when CHIR alone was used compared to using Activin A and BMP4 in combination with CHIR (ABC) to generate a population of NCAM+/CXCR4 low positive-mesoderm progenitor cells (FIG. 2A). It was observed that Activin A and BMP4 in addition to CHIR during mesoderm induction resulted in a decreased percentage of CXCR4+ progenitors compared to CHIR alone. For CHIR only, 7 μM of CHIR99021 was added. For ABC conditions, 9 ng/mL Activin A, 5 ng/mL BMP4, and 7 μM CHIR99021 (Table 2) were added on Day 1 and Activin A and BMP4 only (Table 3) were added on Day 2 of differentiation.

Figure 3A:
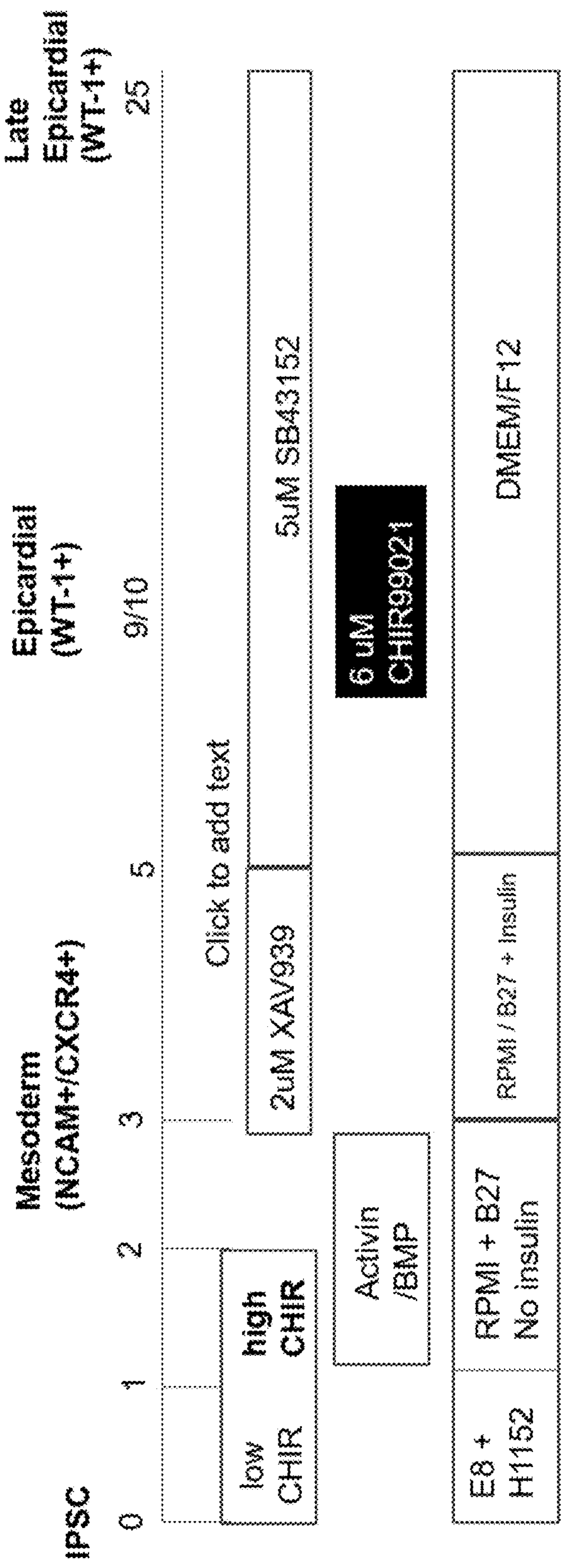
FIGS. 3A-3E.
Figure 3B:
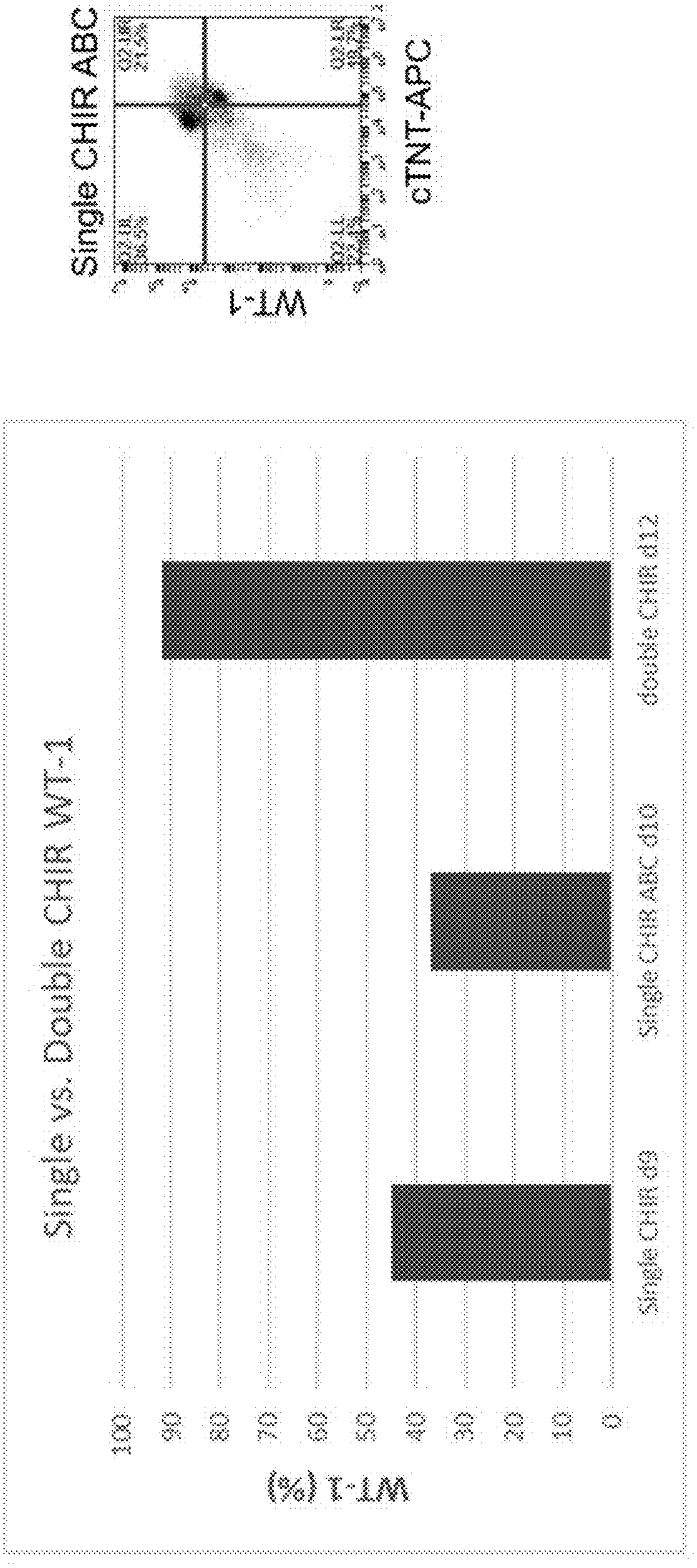
Figure 3C:
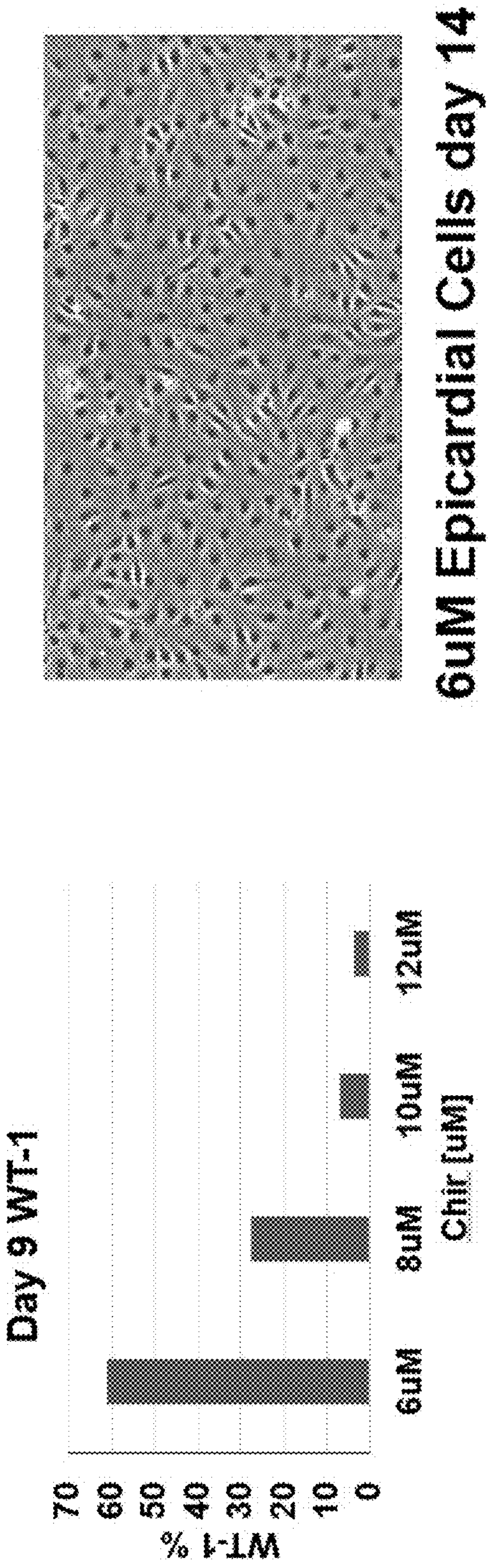
Figure 3D:
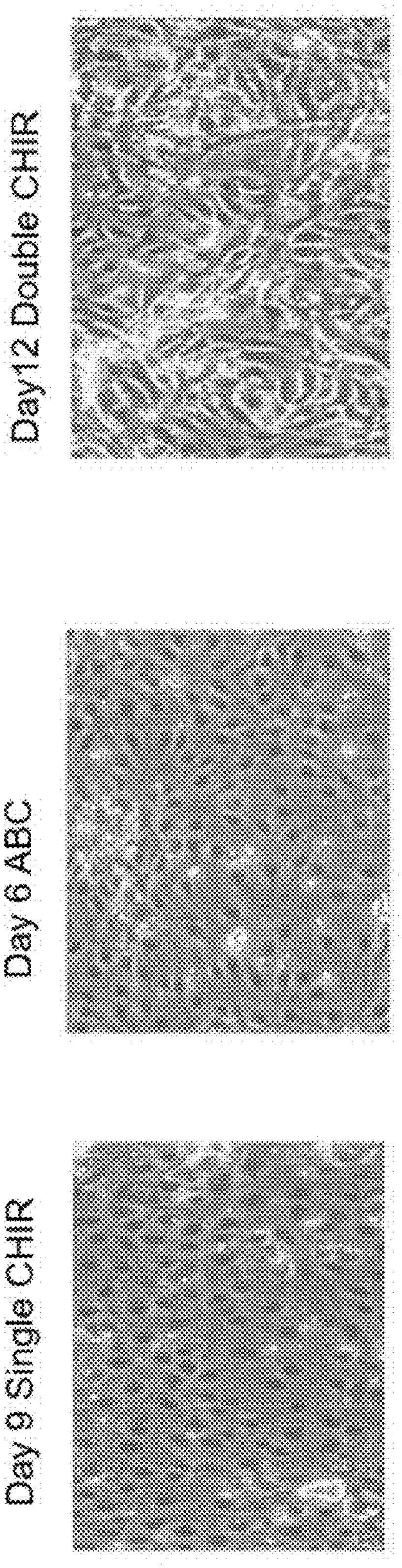
Figure 3E:
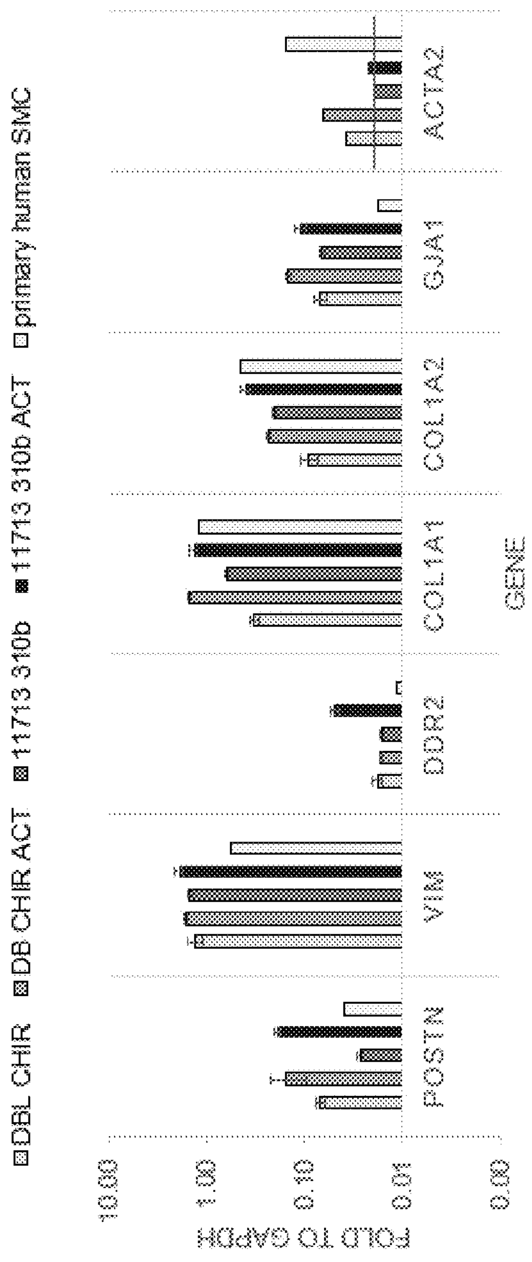

Cardiac mesoderm cells were then dissociated and contacted with a low concentration of Wnt inhibitor, XAV939, (Table 4) for two days to be specified into a WT1 epicardial lineage (FIG. 3A). The percentage of epicardial cells were measured in single CHIR, ABC, and double CHIR conditions. Epicardial induction with single CHIR or ABC step produced a mixed population of epicardial cells and cardiomyocytes. The percentage of WT1+ epicardial cells ranged from 30% WT1 to 90% WT1. These epicardial progenitors were used directly for cardiac fibroblast induction without additional passaging or purification of epicardial cells.

A dose titration of CHIR was performed on iPS cells. It was found that increasing the dose of CHIR on Day 1 in the single CHIR method did not increase the percentage of WT1+ epicardial cells on Day 9 (FIG. 3B). A dose of 6 μM CHIR on Day 1 generated a population of 60% WT1 epicardial progenitor cells that have characteristic cobblestone morphology by Day 14 (FIG. 3C).

Single CHIR treated epicardial cells were observed to have a flattened cobblestone morphology and a pronounced round large nucleus (FIG. 3C). When Activin and BMP were added with the single CHIR, the epicardial cells retained a flattened cobble stone morphology and dark, round nucleus. Cell-cell borders became less pronounced. There was no need to passage the epicardial cells. Notably, with the secondary CHIR applied at the epicardial stage, epicardial progenitors proliferated dramatically. This was visible by increased cell numbers, decreased cell size, and more elongated morphology. Flow cytometry at D12 showed Double CHIR epicardial cells had >90% WT-1 purity, while WT-1 was lower in D9 ABC single CHIR, ranging from 30-80%, and more similar to CHIR only. In these studies, the ABC progenitor cells did not proliferate extensively and need to be passaged like the Double CHIR cells.

Cardiac fibroblasts were induced in serum containing conditions on Day 25. The cells were fed DMEM-Low glucose, 10% FBS, Ascorbic Acid, and 200 ng/mL basic FGF and purified through successive passaging (Table 6). Cardiac fibroblasts were >85% positive for TE-7 and CD29 and quiescent (i.e., less than 5% αSMA) (FIG. 4A).

Increasing concentrations of basic FGF were observed to increase the percentage of CD29 positive cells during cardiac fibroblast differentiation of epicardial progenitors from the ABC method (FIG. 4B).

Seven independent iPSC lines were differentiated to cardiac fibroblasts using ABC conditions during mesoderm induction and cardiac fibroblast specification in serum-containing medium with high levels of basic FGF. All of the cardiac fibroblasts had high fibroblast purity (TE-7) and were quiescent having less than 5% alpha smooth muscle actin purity (αSMA) (FIG. 4C).

In another method, cardiac fibroblasts were differentiated from the ABC epicardial progenitors under serum free conditions (Table 7). Cardiac fibroblasts were induced from epicardial cells by culturing in serum-free medium without TGFβ inhibitor for 5 passages. The cardiac fibroblasts induced in serum free media had high TE-7 purity (>85%) and were quiescent (αSMA <5%) by flow cytometry (FIG. 4D). The cardiac fibroblasts were cryopreserved between passage 5 and passage 7.

The cardiac fibroblasts were thawed and plated on vitronectin-coated plates at 10 k/cm$^2$ and activated with TGFβ. TGFβ was added at 20 ng/mL or 40 ng/mL to activate cardiac fibroblasts on Day 2, with a media change on Day 4. On Day 5, media supernatants were collected and analyzed for fibronectin secretion by a Human FN ELISA Kit Cat #BMS2028. On Day 3 and Day 5, cardiac fibroblasts were harvested and counted by ViCell-XR. After 5 days cells were collected for flow cytometry. An alpha smooth muscle actin expressing population was seen to emerge in the presence of TGFβ (FIG. 4E).

For the cardiac tri-culture microtissue assay, cryopreserved iPSC-derived cell types were combined in a specific ratio and formed into microtissues in microwell plates (FIG. 5A). Microtissues containing 65% iCell Cardiomyocytes, 20% iCell Endothelial cells, and 15% iPSC derived cardiac fibroblasts are shown in FIG. 5B. After 1-2 days, the microtissues were contracting.

Microtissues were fed a co-culture medium (Table 8) to support all three cell types. Fourteen days post assembly, microtissues were observed to respond to challenge with inotropic compounds. The isogenic tri-culture cardiac microtissues exhibited inotropic response to beta-adrenergic agonist isoproterenol across iPSC cardiac fibroblast clones, lot of cardiac fibroblasts, and donor lines (FIG. 6A). Microtissues were generated from three donor lines 11713, 01279, and 01434. Microtissues contained either iPSC-derived cardiomyocytes only or were tri-culture, containing isogenic iPSC-derived cardiomyocytes, iPSC-derived endothelial cells, and iPSC-derived cardiac fibroblasts. All microtissues were assayed for response to isoproterenol on Day 14 of culture. An increase in calcium transient amplitude was observed only in tri-culture microtissues and not in cardiomyocyte only microtissues. This response was in tri-culture microtissues from all three donor lines, in two independently produced lots of cardiac fibroblasts from donor 01434, and in microtissues containing cardiac fibroblasts from two independently derived clones from donor 11713 (11713.008 and 11713.847).

Increasing inotropic response was observed with increasing cardiac fibroblasts in tri-culture microtissues (FIG. 6B). Cardiac fibroblast concentration was found to impact ionotropic response of tri-culture microtissues. Response to dobutamine (DOB), digoxin (DIG), isoproterenol (ISO), and epinephrine (EPI) were assessed at DIV 14 on cardiac tri-culture microtissues comprised of 10,000 total cells and 20% iCell Endothelial Cells and iCell Cardiomyocytes and varying concentrations of iPSC derived cardiac fibroblasts (CF). Increased CF content in cardiac 3D microtissues led to increased calcium amplitude inotropic response to dobutamine, digoxin, and epinephrine. (FIG. 6B).

Compound library screening can be performed with cardiac tri-culture microtissues for cardiovascular drug discovery. Small numbers of cells were used in multiwell plates (e.g., 96, 384, or 1536) across numerous high-throughput assay platforms (FIG. 7A).

Hypoxia was observed to bring out the disease phenotype in the dilated cardiomyopathy (CM) model LMNAL35P microtissues. Tri-culture microtissues were made from Normal Healthy Control (NHC), isogenic LMNA corrected, and isogenic LMNA-L35P iPSC-derived cell types. After cells were beating, cells were placed in hypoxia (5% $O_2$) or normoxia (20% $O_2$). Normal healthy control microtissue, and isogenic LMNA mutation corrected microtissues had similar beat rates in normoxia and hypoxia while LMNA mutant tri-culture MT had significantly slower beat rate in hypoxia (FIG. 7A).

Figure 8A:
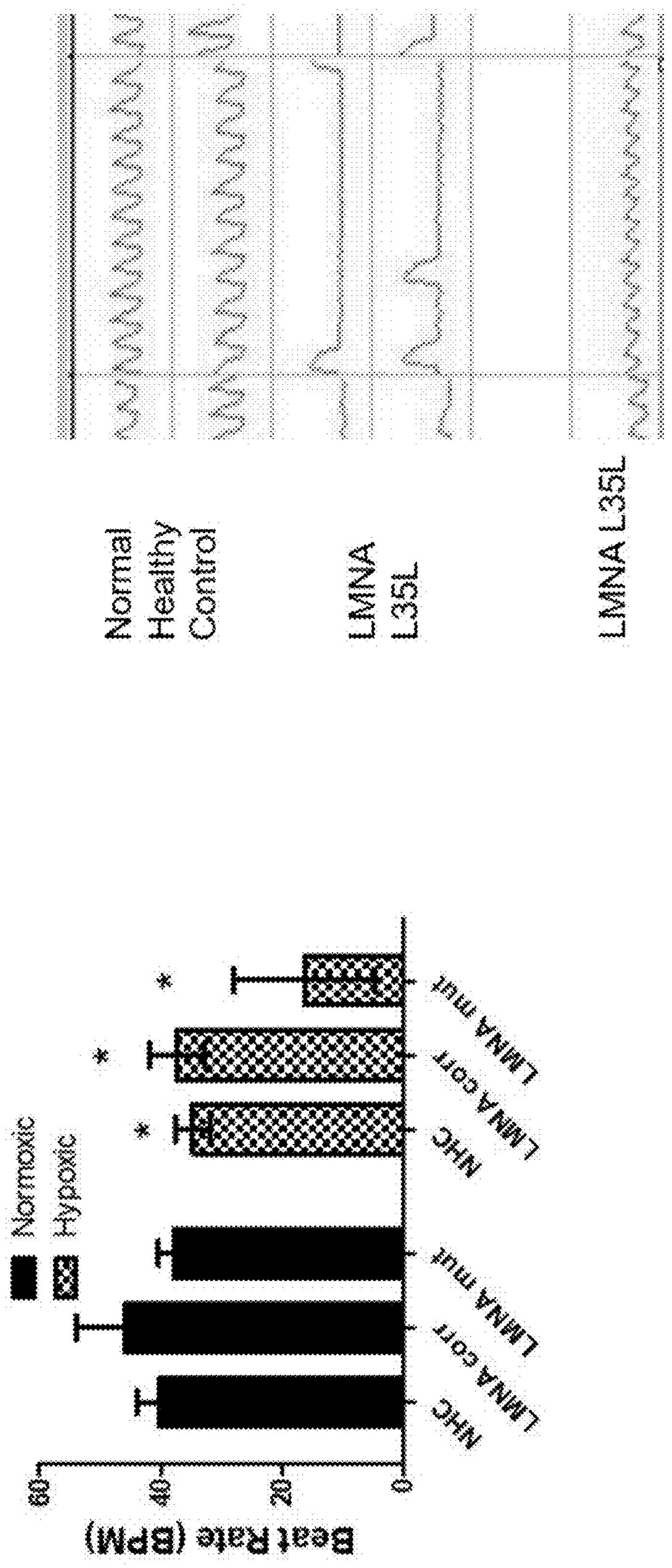
FIGS. 8A-8B.
Figure 8B:
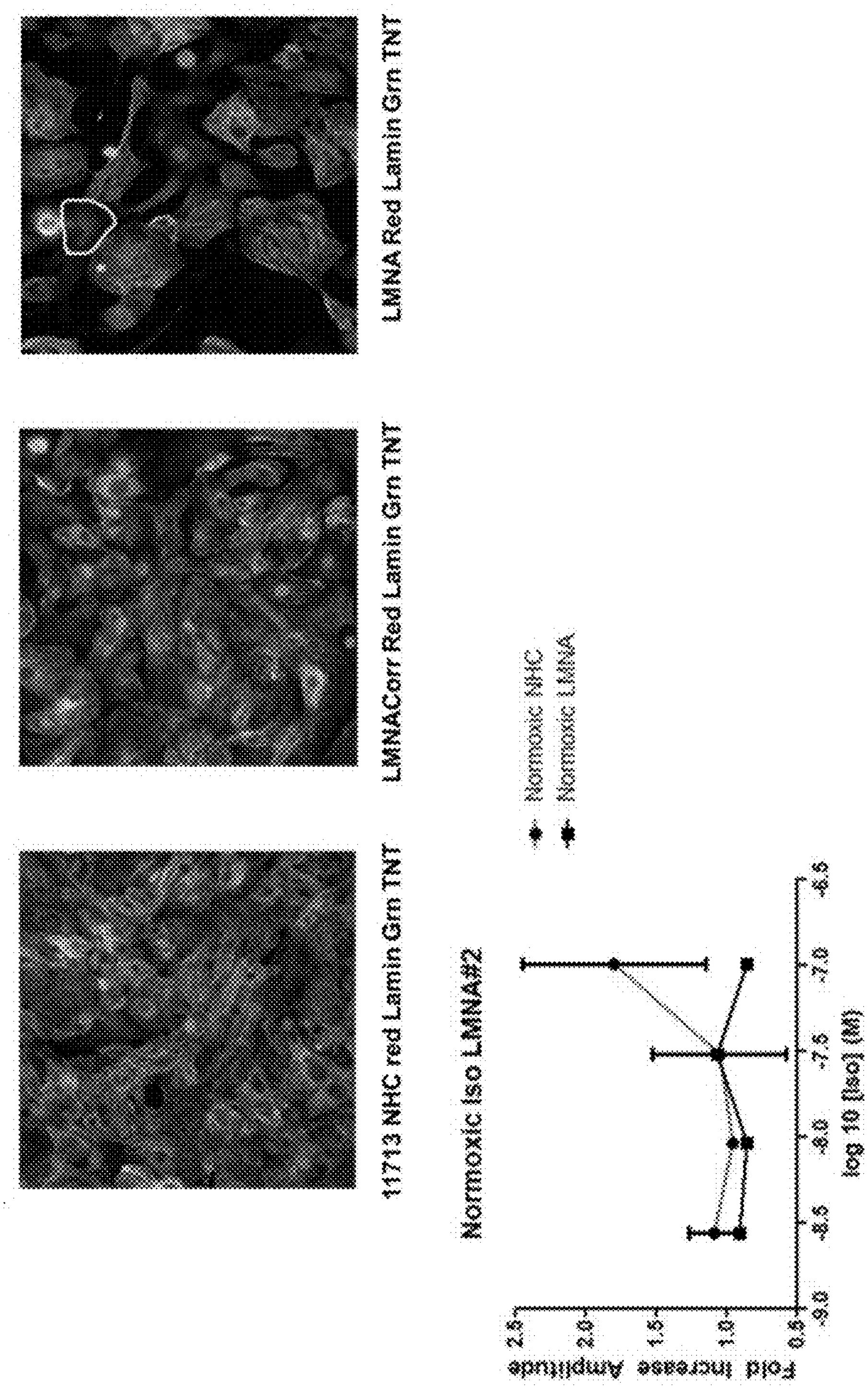

Microtissues from dilated cardiomyopathy mutation LMNAL35P did not respond to inotropic compound. Tri-culture microtissues were made from Normal Healthy Control (NHC) and isogenic LMNA-L35P iPSC-derived cell types. Fourteen days post microtissue formation, microtissues were challenged with isoproterenol. Microtissues from normal healthy donor iPSC responded with an increase in calcium transient amplitude at 100 nM isoproterenol. The disease model microtissue did not respond to increased isoproterenol (FIG. 8).

Thus, the present studies were shown to produce highly pure populations of cryopreserved quiescent cardiac fibroblasts (>75% TE-7, <5% αSMA) from a population of (WT1+) epicardial cells in serum or serum-free conditions. These cardiac fibroblasts were observed to have isotropic response to isoproterenol when in a co-culture with cardiomyocytes and endothelial cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Amit et al., *Dev. Bio.,* 227:271-278, 2000.

Archer, 2018

Byrne et al., *Nature,* 450(7169):497-502, 2007.

Dunn et al., *Drugs* 61:1957, 2001.

Fernandes, et al., *J. Biotechnology,* 132(2):227-236, 2007.

Guo and Pu et al., 2020

International Patent Publication No. PCT/JP2009/062911

International Patent Publication No. PCT/JP2011/069588

International Patent Publication No. WO 02/44343

International Patent Publication No. WO 03/050251

International Patent Publication No. WO 2007/069666

International Patent Publication No. WO2005/123902

International Patent Publication No. WO98/30679

Keller et al., *Curr. Opin. Cell Biol.,* 7:862-869, 1995.

Klimanskaya et al., *Lancet.,* 365: P1636-1641, 2005.

Ludwig et al., *Nat. Biotechnol.,* 24:185-187, 2006b.

Ludwig et al., *Nat. Methods,* 3:637-646, 2006a.

Ravenscroft, 2016

Takahashi et al., *Cell,* 131, 861-872, 2007.

Thomson and Marshall, *Curr. Top. Dev. Biol.,* 38:133-165, 1998.

Thomson and Odorico, *Trends Biotechnol.,* 18(2):53-57, 2000.

Thomson et al. *Proc. Natl. Acad. Scie. USA,* 92:7844-7848, 1995.

U.S. application Ser. No. 12/478,154

U.S. Pat. No. 8,546,140

U.S. Pat. No. 5,843,780

U.S. Pat. No. 6,103,470

U.S. Pat. No. 6,110,739

U.S. Pat. No. 6,200,806
U.S. Pat. No. 6,280,718
U.S. Pat. No. 6,416,998
U.S. Pat. No. 7,029,913
U.S. Pat. No. 7,442,548
U.S. Pat. No. 7,598,364
U.S. Pat. No. 7,989,425
U.S. Pat. No. 8,058,065
U.S. Pat. No. 8,071,369
U.S. Pat. No. 8,129,187
U.S. Pat. No. 8,183,038
U.S. Pat. No. 8,268,620
U.S. Pat. No. 8,546,140
U.S. Pat. No. 8,691,574
U.S. Pat. No. 8,741,648
U.S. Pat. No. 8,900,871
U.S. Pat. No. 9,175,268
U.S. Patent Publication No. 2003/0211603
U.S. Patent Publication No. 2009/0246875
U.S. Patent Publication No. 2010/0210014
U.S. Patent Publication No. 2011/0104125
U.S. Patent Publication No. 2012/0276636
U.S. Patent Publication No. 2015/0191697
U.S. Patent Publication No. US 2002/0086005
United States Patent 20070116680
Watanabe et al., *Nature Neurosci.,* 8:288-296, 2005.
Wobus et al., *Ann. N.Y. Acad. Sci.,* 27:752, 1995.
Xu et al., *Nat. Biotechnol.,* 19:971-974, 2001.
Yu et al., *Science,* 318: 1917-1920, 2007.

What is claimed is:

1. An in vitro method for producing human pluripotent stem cell (PSC)-derived cardiac fibroblast progenitor cells comprising:

(a) culturing PSC aggregates in media comprising a Wnt agonist, Activin agonist, and BMP4 for mesoderm induction for about one day;

(b) further culturing the PSC aggregates in media comprising an Activin agonist and BMP4 and essentially free of a Wnt agonist for about 1-3 days to produce a population of mesoderm progenitor cells that are positive for NCAM and have low expression of CXCR4 ($NCAM+/CXCR4^{low}$); and (c) culturing the mesoderm progenitor cells in media comprising a Wnt inhibitor for about 1-3 days to produce a population of cardiac fibroblast progenitor cells, wherein the cardiac fibroblast progenitor cells comprise epicardial progenitor cells, endothelial fibroblast progenitor cells, and second heart field progenitors.

2. The method of claim 1, wherein the media of step (b) is free of a Wnt agonist.

3. The method of claim 1, wherein less than 10% of the mesoderm progenitor cells are positive for CXCR4.

4. The method of claim 1, wherein the cardiac fibroblast progenitor cells comprise epicardial progenitor cells, endothelial fibroblast progenitor cells, second heart field progenitors, and neural crest progenitor cells.

5. The method of claim 1, wherein about 30% to 70% of the cardiac fibroblast progenitors cells are second heart field progenitor cells.

6. The method of claim 5, wherein the second heart field progenitor cells are positive for GATA4 and/or HAND2.

7. The method of claim 1, wherein about 10-50% of the cardiac fibroblast progenitor cells are endothelial fibroblast progenitor cells.

8. The method of claim 7, wherein the endothelial fibroblast progenitor cells are positive for TEK.

9. The method of claim 1, wherein about 5-40% of the cardiac fibroblast progenitor cells are epicardial progenitor cells.

10. The method of claim 9, wherein the epicardial progenitor cells are positive for WT1, SNAI1, TBX19, and/or TBX20.

11. The method of claim 1, wherein step (c) is further defined as producing a mixed population of cardiac fibroblast progenitor cells and cTNT+ cardiomyocytes.

12. The method of claim 1, further comprising producing PSC-derived cardiac fibroblasts comprising further differentiating the cardiac fibroblast progenitor cells to produce a population of cardiac fibroblasts in media comprising basic FGF (bFGF).

13. The method of claim 12, wherein the differentiating is performed in the absence of a TGFβ inhibitor.

14. The method of claim 12, wherein the cardiac fibroblasts express vimentin (VIM), COL1A1, COL1A2, discoidin domain receptor 2 (DDR2), periostin (POSTN), and/or secreted protein acidic and rich in cysteine (SPARC).

15. The method of claim 12, wherein the cardiac fibroblasts are at least 50% positive for GATA-4 and/or at least 85% positive for CD90.

16. The method of claim 12, wherein the media of step (b) is free of or essentially free of TGFβ inhibitor.

17. The method of claim 12, wherein the population of cardiac fibroblasts comprises at least 75% cells positive for TE-7, CD29 and/or CD90.

18. The method of claim 12, wherein the population of cardiac fibroblasts comprises at least 85% cells positive for TE-7 and CD29 and less than 5% cells positive for αSMA.

19. The method of claim 12, further comprising culturing the population of cardiac fibroblasts in the presence of TGFβ to produce a population of activated cardiac fibroblasts.

20. The method of claim 1, wherein the PSCs are induced pluripotent stem cells (iPSCs) or embryonic stem cells (ESCs).

21. The method of claim 1 wherein the PSCs are derived from a subject with dilated cardiomyopathy and comprise an LMNA-L35P mutation.

22. The method of claim 1, wherein the population of cardiac fibroblast progenitor cells in step (c) comprise at least 30% WT1+ progenitor cells.

23. The method of claim 1, wherein the Wnt agonist is present at a concentration of about 5-10 μM, the Activin agonist is present at a concentration of 5-20 ng/ml, and the BMP4 is present at a concentration of about 0.1 ng/mL to 10 ng/ml in the media of step (a).

24. The method of claim 1, wherein the Wnt agonist is CHIR 99021, IWP-1, IWP-2, IWP-3, IWP-4, CAS 853220-52-7 (2-Amino-4-(3,4-(methylenedioxy) benzylamino)-6-(3-methoxyphenyl) pyrimidine), SB216763, CHIR 98014, TWS119, Tideglusib, SB415286, BIO, AZD2858, AZD1080, AR-A014418, TDZD-8, LY2090314, or IM-12.

25. The method of claim 1, wherein the Activin agonist is Activin A, Activin B, Activin AB, TGFβ1, Growth and Differentiation Factor (GDF)-3, BML-284 or Nodal.

26. The method of claim 1, wherein the Activin agonist is present at a concentration of 5-20 ng/ml and the BMP4 is present at a concentration of about 0.1 ng/ml to 10 ng/ml in the media of step (b).

27. The method of claim 1, wherein the Wnt inhibitor is XAV939, ICG-001, IWR-1-endo, Wnt-C59, LGK-974, LF3, CP21R7, NCB-0846, PNU-74654, IWR-1, IWR-2, IWR-3, IWR-4 or KYA179K.

28. The method of claim 1, wherein the Wnt inhibitor is present at a concentration of 1-10 μM in the media of step (c).

29. The method of claim 1, wherein the PSC aggregates of step (a) were obtained by culturing PSCs in the presence of a Wnt agonist and a Rho-associated kinase (ROCK) inhibitor or myosin II inhibitor for about 1 day.

30. The method of claim 29, wherein the Wnt agonist is CHIR 99021, SB216763, CHIR 98014, TWS119, Tideglusib, SB415286, BIO, AZD2858, AZD1080, AR-A014418, TDZD-8, LY2090314, or IM-12.

31. The method of claim 29, wherein the Wnt agonist is present at a concentration of 1-5 μM.

32. The method of claim 1, wherein the media of step (c) is free of or essentially free of BMP4, a Wnt agonist, and retinoic acid.

* * * * *